United States Patent
Tsuchiya et al.

(10) Patent No.: US 9,165,355 B1
(45) Date of Patent: Oct. 20, 2015

(54) INSPECTION METHOD

(71) Applicant: NuFlare Technology, Inc., Yokohama (JP)

(72) Inventors: Hideo Tsuchiya, Tokyo (JP); Manabu Isobe, Kanagawa (JP); Hiroteru Akiyama, Kanagawa (JP); Makoto Yabe, Kanagawa (JP); Takafumi Inoue, Kanagawa (JP); Nobutaka Kikuiri, Tokyo (JP)

(73) Assignee: NuFlare Technology, Inc., Yokohama (JP)

( * ) Notice: Subject to any disclaimer, the term of this patent is extended or adjusted under 35 U.S.C. 154(b) by 65 days.

(21) Appl. No.: 14/208,757

(22) Filed: Mar. 13, 2014

(51) Int. Cl.
G06K 9/00 (2006.01)
G06T 7/00 (2006.01)
G06K 9/62 (2006.01)

(52) U.S. Cl.
CPC ............ *G06T 7/0006* (2013.01); *G06K 9/6215* (2013.01); *G06T 7/001* (2013.01); *G06T 7/0008* (2013.01); *G06T 7/0044* (2013.01); *G06T 2200/24* (2013.01); *G06T 2207/30108* (2013.01); *G06T 2207/30148* (2013.01); *G06T 2207/30168* (2013.01)

(58) Field of Classification Search
None
See application file for complete search history.

(56) References Cited

U.S. PATENT DOCUMENTS

| | | | | |
|---|---|---|---|---|
| 7,415,149 B2* | 8/2008 | Tsuchiya et al. | ............... | 382/144 |
| 7,421,109 B2* | 9/2008 | Tsuchiya et al. | ............... | 382/144 |
| 7,551,767 B2* | 6/2009 | Tsuchiya et al. | ............... | 382/144 |
| 2007/0127806 A1* | 6/2007 | Tsuchiya et al. | ............... | 382/144 |
| 2007/0156379 A1* | 7/2007 | Kulkarni et al. | ................ | 703/14 |
| 2007/0230770 A1* | 10/2007 | Kulkarni et al. | ............... | 382/149 |
| 2007/0288219 A1* | 12/2007 | Zafar et al. | ........................ | 703/14 |
| 2008/0166054 A1* | 7/2008 | Tsuchiya et al. | ............... | 382/194 |
| 2013/0279792 A1* | 10/2013 | Hess et al. | ..................... | 382/145 |
| 2014/0294283 A1* | 10/2014 | Takeda et al. | ................. | 382/144 |
| 2014/0307254 A1* | 10/2014 | Yamashita et al. | ......... | 356/237.5 |
| 2015/0005917 A1* | 1/2015 | Yiin et al. | ..................... | 700/109 |

FOREIGN PATENT DOCUMENTS

| | | |
|---|---|---|
| JP | 3824542 | 9/2006 |
| JP | 4236825 | 3/2009 |
| JP | 4564768 | 10/2010 |

OTHER PUBLICATIONS

U.S. Appl. No. 14/607,483, filed Jan. 28, 2015, Kikuiri, Spec, Drawings, Claims Only.

* cited by examiner

Primary Examiner — Aaron W Carter
(74) Attorney, Agent, or Firm — Oblon, McClelland, Maier & Neustadt, L.L.P.

(57) ABSTRACT

An inspection method comprising, virtually dividing a sample, in which a plurality of chip patterns are formed, into a plurality of strip-shaped stripes along a predetermined direction to acquire an optical image of the chip pattern in each of the stripes, performing filtering based on design data of the chip pattern to produce a reference image corresponding to the optical image, comparing the chip pattern using a die-to-database method and comparing a repetitive pattern portion in the chip pattern using a cell method, obtaining at least one of a dimension difference and a dimension ratio between a pattern of the optical image and a pattern of the reference image compared to the pattern of the optical image by the die-to-database method; and obtaining a dimension distribution of the plurality of chip patterns from at least one of the dimension difference and the dimension ratio.

12 Claims, 12 Drawing Sheets

INSPECTION METHOD

CROSS-REFERENCE TO THE RELATED APPLICATION

The entire disclosure of the Japanese Patent Application No. 2013-055500, filed on Mar. 18, 2013 including specification, claims, drawings, and summary, on which the Convention priority of the present application is based, are incorporated herein in its entirety.

FIELD OF THE INVENTION

The present invention relates to an Inspection Method.

BACKGROUND

With high integration and large capacity of a Large Scale Integration (LSI), a circuit dimension required for a semiconductor element becomes increasingly narrowed. For example, a pattern having a line width of several tens of nanometers is required to be formed in the latest typical logic device.

It is necessary to improve a production yield of the expensive LSI in a production process. In the semiconductor element, during a production process, an original design pattern (that is, a mask or a reticle, hereinafter collectively referred to as a mask) in which a circuit pattern is formed is exposed and transferred onto a wafer by a reduction projection exposure apparatus called a stepper or a scanner. A shape defect of a mask pattern can be cited as a large factor that reduces a production yield of the semiconductor element.

The finer the dimensions of an LSI pattern formed on the wafer becomes, the smaller the shape defect of the mask pattern becomes. As fluctuations of various process conditions are absorbed by enhancing dimensional accuracy of the mask, it is necessary to defect the defect of the extremely small pattern in a mask inspection. At this point, it is also necessary to determine the defect in consideration of the fluctuation in line width dimension or position shift amount of the pattern in a mask surface. For example, Japanese Patent No. 4236825 discloses an inspection apparatus that can detect the fine defect in the mask.

Examples of defect detection techniques include a die-to-database comparison method and a die-to-die comparison method. In the die-to-database comparison method, a reference image generated from design pattern data used in mask production and an optical image of the actual pattern in the mask are compared to each other. In the die-to-die comparison method, in the case that multiple chips having identical pattern configuration are disposed in a part or the whole of the identical mask, the optical images having the identical pattern in chips of the different masks are compared to each other.

A cell comparison method can also be cited as another defect detection technique. The cell comparison method is effectively used in the case that a repetitive pattern called a cell exists in the mask. In the die-to-die comparison method, the chips repetitively formed in the mask are compared to each other. On the other hand, in the cell comparison method, the repetitive patterns such as memory mats, namely, the cells are compared to each other in one chip. For example, the defect is inspected by the cell comparison method in a memory cell group of a DRAM (Dynamic Random Access Memory) element in which the repetitive pattern is formed. On the other hand, a logic element in which the repetitive pattern does not exist is inspected by the die-to-die comparison method in which the pattern of the logic element is compared to the pattern of a dummy logic element in an inspection dummy pattern provided at a predetermined position in the mask. Nowadays, with increasing demand for an embedded memory in logic, sometimes both the die-to-die comparison method and the cell comparison method are performed in a one-time inspection process (for example, see Japanese Patent No. 4564768).

The conventional mask inspection is aimed at the detection of the shape defect of the pattern, and a defect determination algorithm suitable for the detection of the shape defect of the pattern and a defect recording method are devised. In the mask inspection apparatus, a function of detecting the defect caused by the fluctuation in line width of the pattern is improved in order to meet a challenge of a lack of an LSI production margin caused by the fluctuation in line width. However, in a contemporary mask pattern, the shape defect or the dimension of the defect determined to be the cause of the fluctuation in line width becomes substantially equal to the fluctuation in line width (line width distribution) in the whole surface of the mask. Therefore, the number of detected defects becomes large.

In a process of generating the reference image in the die-to-database comparison method, filtering the optical image of a typical pattern position in the mask, namely, the learning process of a filter coefficient is performed to the design pattern data, whereby the reference image becomes the pattern image having a line width tendency imitating the pattern line width of a region where the learning process is performed. Therefore, the line width dimension has a distribution in the mask even in the die-to-database comparison method, and the optical image and the reference image are compared to each other with a line width bias (deviation) of the pattern in inspecting the region having the pattern line width different from the pattern line width of the region where the learning process is performed. As a result, the shape defect to be detected or the fluctuation in line width cannot be detected, or the shape and line width that do not need the detection is detected as the defect.

Additionally, in the die-to-die comparison method, the patterns having the line width bias (deviation) are compared to each other when the chips in the regions having the different line widths are compared to each other. Accordingly, the defect to be detected cannot be detected, or the shape and line width that do not need the detection is detected as the defect.

An object of the invention is to provide an inspection method, able to reduce the detection of the unnecessary defect while detecting the defect to be detected.

Other challenges and advantages of the present invention are apparent from the following description.

SUMMARY OF THE INVENTION

According to one aspect of the present invention, an inspection method comprising, virtually dividing a sample, in which a plurality of chip patterns are formed, into a plurality of strip-shaped stripes along a predetermined direction to acquire an optical image of the chip pattern in each of the stripes, performing filtering based on design data of the chip pattern to produce a reference image corresponding to the optical image, comparing the chip pattern using a die-to-database method and comparing a repetitive pattern portion in the chip pattern using a cell method, obtaining at least one of a dimension difference and a dimension ratio between a pattern of the optical image and a pattern of the reference image compared to the pattern of the optical image by the die-to-database method, and obtaining a dimension distribution of the plurality of chip patterns from at least one of the dimension difference and the dimension ratio, wherein, with respect to a position determined to be a defect by the comparison of the die-to-database method, a result of the die-to-database method is stored when a dimension distribution from the position to a preceding position where at least one of the dimension difference and the dimension ratio is obtained falls within a predetermined range by comparing the dimension distribution to a dimension distribution in the stripe including the position determined to be the defect, or a dimension distribution of the chip pattern assumed from the stripe in which the dimension difference is acquired in advance of the stripe concerned, and a result of the cell method is stored instead of the result of the die-to-database method when the dimension distribution from the position determined to be the defect to the preceding position where at least one of the dimension difference and the dimension ratio is obtained exceeds the predetermined range by comparing the dimension distribution to the dimension distribution in the stripe including the position determined to be the defect, or the dimension distribution of the chip pattern assumed from the stripe in which the dimension difference is acquired in advance of the stripe concerned.

Further to this aspect of the present invention, an inspection method, wherein the result of the die-to-database method is stored irrespective of the dimension distribution from the position determined to be the defect to the preceding position, where at least one of the dimension difference and the dimension ratio is obtained, when the result of the cell comparison does not exist because the repetitive pattern portion does not exist in the position determined to be the defect by the comparison of the die-to-database method.

Further to this aspect of the present invention, an inspection method, wherein the dimension difference is a difference in line width between the pattern of the optical image and the pattern of the reference image or a difference of a distance between the patterns of the optical image and a distance between the patterns of the reference image.

Further to this aspect of the present invention, an inspection method, wherein the dimension ratio is a line width ratio of the pattern of the optical image and the pattern of the reference image, or a ratio of a distance between the patterns of the optical image and a distance between the patterns of the reference image.

In another aspect of the present invention, an inspection method comprising, acquiring an optical image of a sample in which a plurality of chip patterns are formed, performing filtering based on design data of the chip pattern to produce a reference image corresponding to the optical image, comparing the chip pattern by a die-to-database method and comparing a repetitive pattern portion in the chip pattern by a cell method, obtaining at least one of a dimension difference and a dimension ratio between a pattern of the optical image, and a pattern of the reference image compared to the pattern of the optical image by the die-to-database method, and obtaining a dimension distribution of the plurality of chip patterns from at least one of the dimension difference and the dimension ratio, wherein, with respect to a position determined to be a defect by the comparison of the die-to-database method, a result of the die-to-database method is stored when a dimension distribution from the position to a preceding position where at least one of the dimension difference and the dimension ratio is obtained falls within a predetermined range by comparing the dimension distribution to a dimension distribution in a chip or a dimension distribution among chips, and a result of the cell method is stored instead of the result of the die-to-database method when the dimension distribution from the position determined to be the defect to the preceding position, where at least one of the dimension difference and the dimension ratio is obtained, exceeds the predetermined range by comparing the dimension distribution to the dimension distribution in the chip or the dimension distribution among the chips.

Further to this aspect of the present invention, an inspection method, wherein the result of the die-to-database method is stored irrespective of the dimension distribution from the position determined to be the defect to the preceding position, where at least one of the dimension difference and the dimension ratio is obtained, when the result of the cell comparison does not exist because the repetitive pattern portion does not exist in the position determined to be the defect by the comparison of the die-to-database method.

Further to this aspect of the present invention, an inspection method, wherein the dimension difference is a difference in line width between the pattern of the optical image and the pattern of the reference image or a difference of a distance between the patterns of the optical image and a distance between the patterns of the reference image.

Further to this aspect of the present invention, an inspection method, wherein the dimension ratio is a line width ratio of the pattern of the optical image and the pattern of the reference image, or a ratio of a distance between the patterns of the optical image and a distance between the patterns of the reference image.

In another aspect of the present invention, an inspection method comprising, virtually dividing a sample in which a plurality of chip patterns are formed into a plurality of strip-shaped stripes along a predetermined direction to acquire an optical image of the chip pattern in each of the stripes, comparing the chip pattern by a die-to-die method and comparing a repetitive pattern portion in the chip pattern by a cell method, obtaining at least one of a dimension difference and a dimension ratio between a pattern of the optical image and a pattern of the reference image compared to the pattern of the optical image by the die-to-die method, and obtaining a dimension distribution of the plurality of chip patterns from at least one of the dimension difference and the dimension ratio, wherein, with respect to a position determined to be a defect by the comparison of the die-to-die method, a result of the die-to-die method is stored when a dimension distribution from the position to a preceding position where at least one of the dimension difference and the dimension ratio is obtained falls within a predetermined range by comparing the dimension distribution to a dimension distribution in the stripe including the position determined to be the defect, or a dimension distribution of the chip pattern assumed from the stripe in which the dimension difference is acquired in advance of the stripe concerned, and a result of the cell method is stored instead of the result of the die-to-die method when the dimension distribution from the position determined to be the defect to the preceding position where at least one of the dimension difference and the dimension ratio is obtained exceeds the predetermined range by comparing the dimension distribution to the dimension distribution in the stripe including the position determined to be the defect or the dimension distribution of the chip pattern assumed from the stripe in which the dimension difference is acquired in advance of the stripe concerned.

Further to this aspect of the present invention, an inspection method, wherein the result of the die-to-die method is stored irrespective of the dimension distribution from the position determined to be the defect to the preceding position whereat least one of the dimension difference and the dimension ratio is obtained, when the result of the cell method does not exist because the repetitive pattern portion does not exist in the position determined to be the defect by the comparison of the die-to-die method.

Further to this aspect of the present invention, an inspection method, wherein the dimension difference is a difference in line width between the patterns of the optical images or a difference in distance between the patterns of the optical images.

Further to this aspect of the present invention, an inspection method, wherein the dimension ratio is a line width ratio of the patterns of the optical images or a ratio of a distance between the patterns of the optical image.

DETAILED DESCRIPTION OF THE EMBODIMENTS

Embodiment 1

Figure 1:
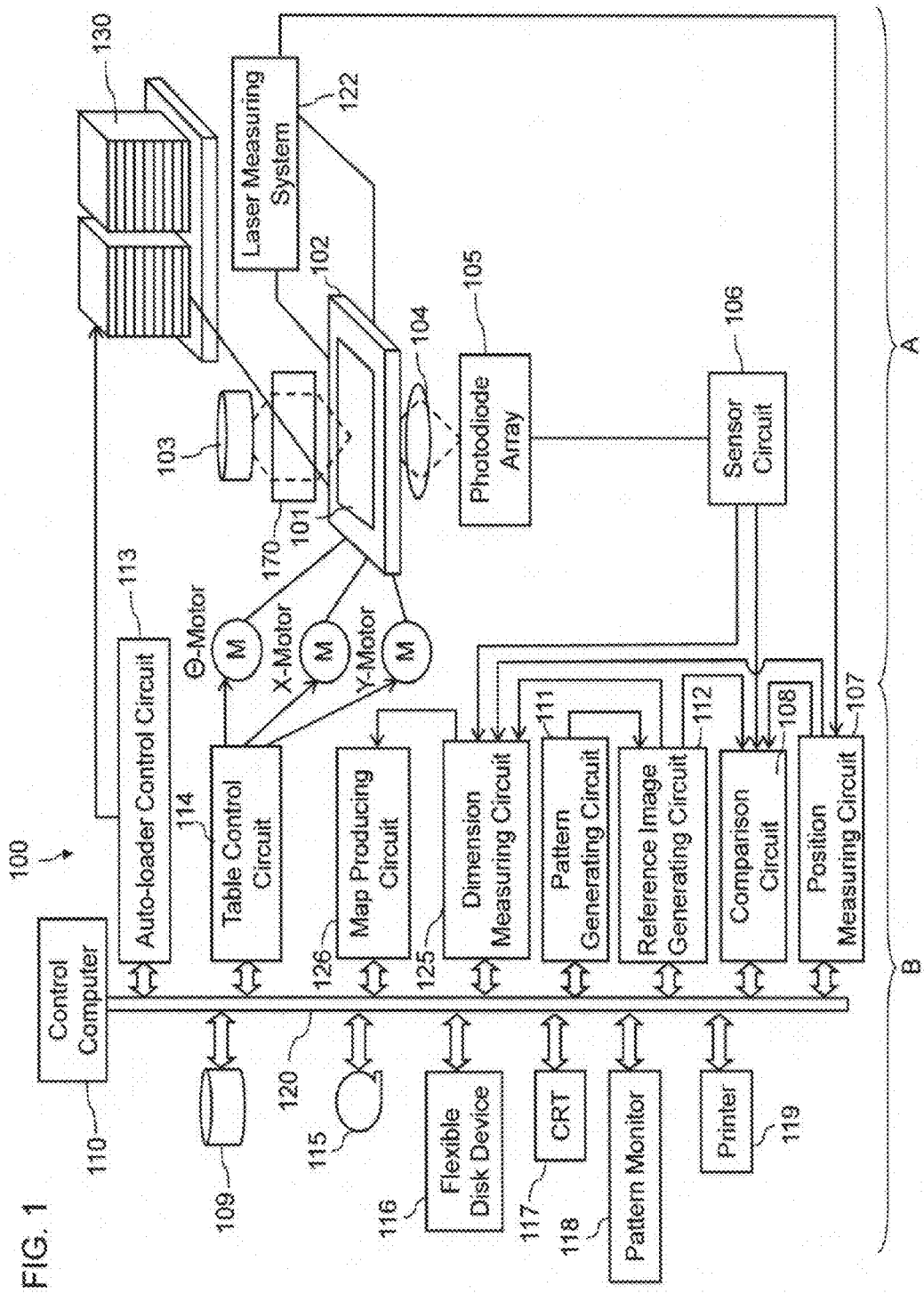
FIG. 1 is a schematic configuration diagram of an inspection apparatus according to a first embodiment and a second embodiment.
Figure 2:
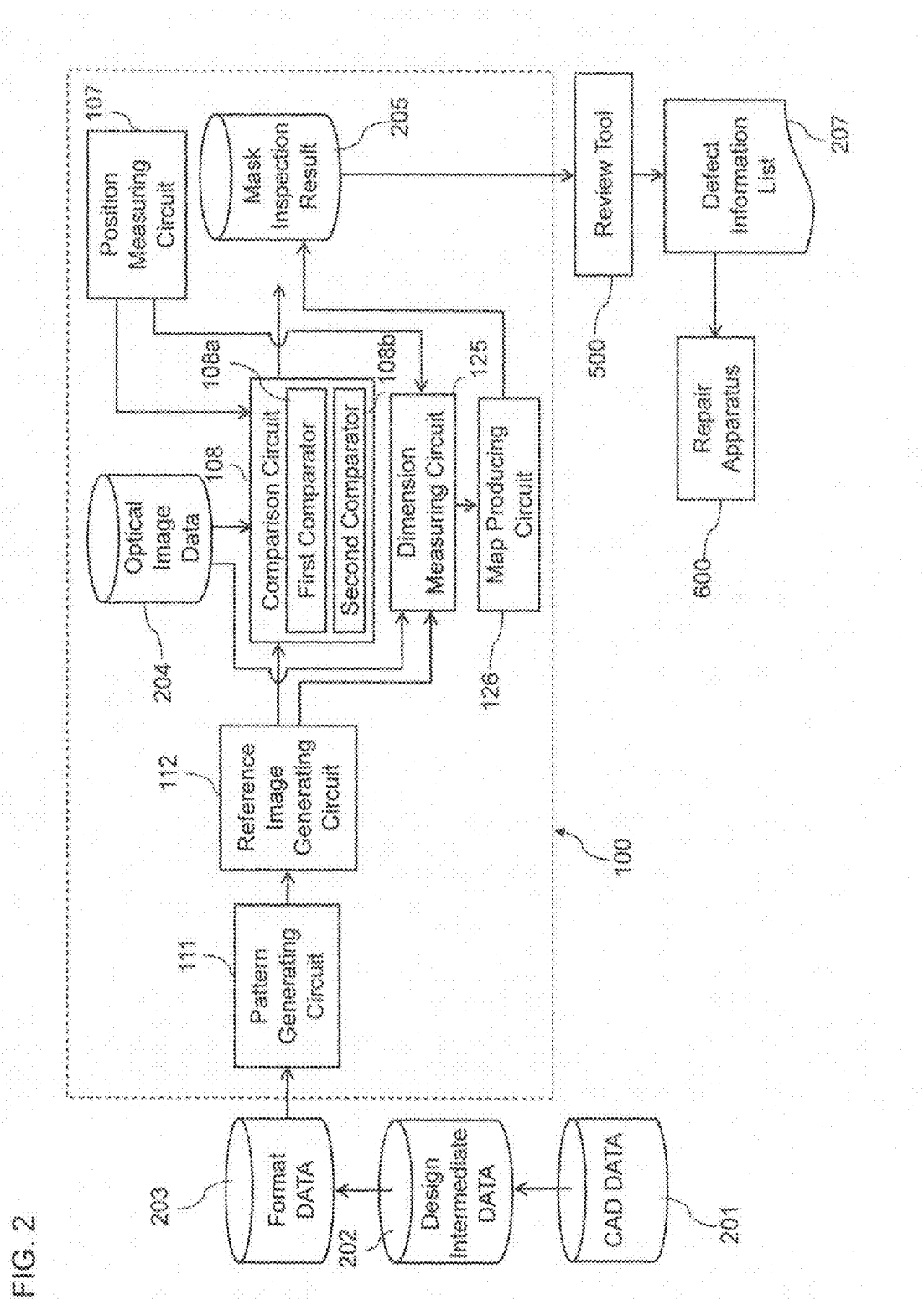
FIG. 2 is a view illustrating a data flow in the inspection apparatus of FIG. 1.

FIG. 1 is a schematic configuration diagram of an inspection apparatus according to a first embodiment. FIG. 2 is a view illustrating a data flow in the inspection apparatus of FIG. 1. In FIGS. 1 and 2, a configuration unit necessary in the first embodiment is illustrated. However, another well-known configuration unit necessary for an inspection may be used. As used herein, a "unit" or "circuit" can be configured by a program operating on a computer. Alternatively, the "unit" or "circuit" may be constructed by not only the program that is software, but also a combination of software, hardware, or firmware. In the case that the "unit" or "circuit" may be constructed by the program, the program can be recorded in a recording device such as a magnetic disk drive.

In the first embodiment, a mask used in photolithography is used as an inspection target. Alternatively, as another example, a wafer may be used as the inspection target.

As illustrated in FIG. 1, an inspection apparatus 100 includes a configuration unit A that constitutes an optical image acquisition unit and a configuration unit B that performs processing necessary for an inspection using an optical image acquired by the configuration unit A.

The configuration unit A includes a light source 103, an XYθ-table 102 that is movable in a horizontal direction (X-direction and Y-direction) and a rotation direction (θ-direction), an illumination optical system 170 that constitutes a transmission illumination system, a magnifying optical system 104, a photodiode array 105, a sensor circuit 106, a laser length measuring system 122, and an auto-loader 130.

In the configuration unit A, the optical image 204 of a mask 101 that becomes an inspection target is acquired. The optical image data 204 is an image of a mask in which a figure pattern is written based on graphic data included in design pattern data of the mask 101. For example, the optical image data 204 is 8-bit data with no code, and expresses a gradation of brightness of each pixel.

Figure 10:
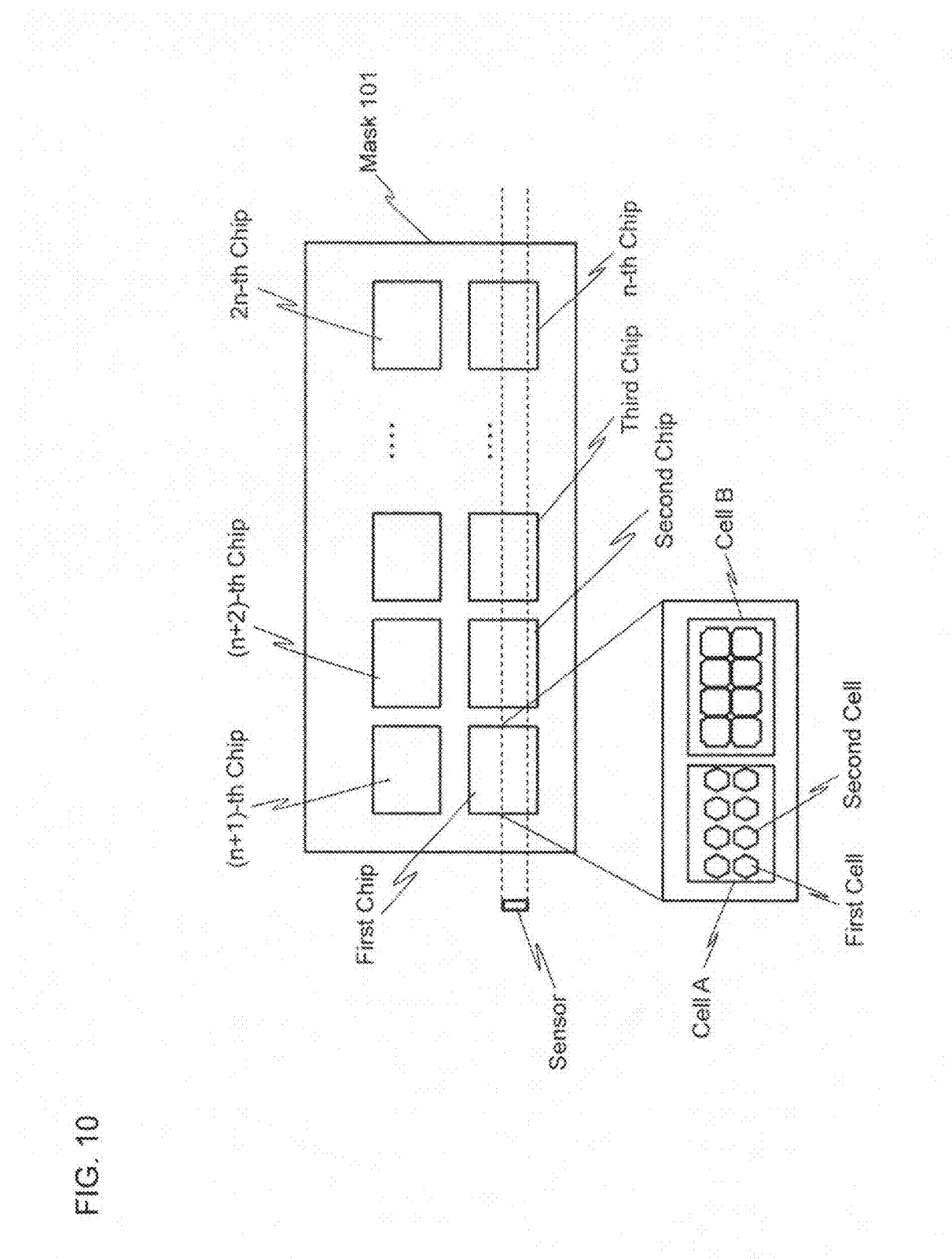
FIG. 10 is an example of a schematic diagram of a chip pattern of a mask.

Multiple chip patterns are formed in the mask 101. FIG. 10 is a partially enlarged schematic diagram illustrating the chip pattern. As illustrated in FIG. 10, $2n$ chip patterns are formed in a region in the mask 101, and cells A and B each of which is formed by a repetitive pattern are formed in each chip pattern.

The auto-loader 130 locates the mask 101 on the XYθ-table 102. An auto-loader control circuit 113 drives the auto-loader 130 under the control of a control computer 110. When the mask 101 is positioned on the XYθ-table 102, the patterns formed in the mask 101 are irradiated with light from the light source 103 disposed above the XYθ-table 102. More particularly, the mask 101 is irradiated with a light emitted from the light source 103 through the illumination optical system 170. The magnifying optical system 104, the photodiode array 105, and the sensor circuit 106 are disposed below the mask 101. The light transmitted through the mask 101 forms the optical image on the photodiode array 105 through the magnifying optical system 104.

The magnifying optical system 104 may be configured such that a focal point is automatically adjusted by an automatic focusing mechanism (not illustrated). Although not illustrated, the inspection apparatus 100 may irradiate the mask 101 with the light from below and guide the reflected light to the photodiode array through the magnifying optical system. In this case, the optical image formed by the transmitted light and reflected light can simultaneously be acquired.

The photodiode array 105 performs photoelectric conversion to the pattern image of the mask 101 formed on the photodiode array 105, and the sensor circuit 106 performs A/D (analog-digital) conversion to the pattern image. A plurality of sensor pixels (not illustrated) is disposed in the photodiode array 105. A TDI (Time Delay Integration) sensor can be cited as an example of the sensor. In this case, the TDI sensor captures the image of the pattern in the mask 101 while the XYθ-table 102 moves continuously. At this point, the light source 103, the enlarging optical system 104, the photodiode array 105, and the sensor circuit 106 constitute a high-magnification inspection optical system.

In the configuration unit B, the control computer 110, that is, the controller controlling the whole of the inspection apparatus 100 is connected to a position measuring circuit 107, a comparison circuit 108 that includes a first comparator 108a and a second comparator 108b, a reference image generating circuit 112 that is an example of the reference image producing unit, an pattern generating circuit 111, a dimension measuring circuit 125 that is an example of the dimension difference/dimension ratio acquisition unit, a map producing circuit 126 that is an example of the dimension distribution acquisition unit, an auto-loader controller 113, a table control circuit 114, a magnetic disk drive 109 that is an example of the storage device, a magnetic tape device 115, a flexible disk drive 116, a CRT 117, a pattern monitor 118, and a printer 119 through a bus 120 that constitutes a data transmission line. The XYθ-table 102 is driven by an X-axis motor, a Y-axis motor, and a θ-axis motor under the control of the table control circuit 114. For example, an air slider, a linear motor, and a step motor can be used as these driving mechanisms and can further be used in any combination with each other.

As described above, the "unit" or "circuit" in FIG. 1 can be configured as a program operating on the computer. Alternatively, the "unit" or "circuit" may be constructed by not only the program that is software, but also a combination of software, hardware, or firmware. In the case that the "unit" or "circuit" may be constructed by the program, the program can be recorded in the magnetic disk drive 109. For example, each of the auto-loader control circuit 113, the table control circuit 114, the comparison circuit 108, and the position measuring circuit 107 may be constructed by an electric circuit, the software that can be processed by the control computer 110, or the combination of the electric circuit and the software.

The control computer 110 controls the table control circuit 114 to drive the XYθ-table 102. A moving position of the XYθ-table 102 is measured by the laser length measuring system 122, and transmitted to the position measuring circuit 107.

The control computer 110 controls the auto-loader control circuit 113 to drive the auto-loader 130. The auto-loader 130 automatically conveys the mask 101, notifies an operator of an end of the inspection, reviews a defect as needed, and automatically discharges the mask 101.

The design pattern data that becomes reference data of the die-to-database method is stored in the magnetic disk drive 109. In the progress of the inspection, the design pattern data is read and transmitted to the pattern generating circuit 111. The design pattern data will be described with reference to FIG. 2.

As illustrated in FIG. 2, CAD data 201 produced by a designer (user) is converted into design intermediate data 202 having a hierarchical format such as OASIS. The design pattern data, which is produced in each layer and formed in the mask, is stored in the design intermediate data 202. At this point, generally the inspection apparatus is configured not to directly read OASIS data. That is, independent format data is used by each manufacturer of an inspection apparatus. For this reason, the OASIS data is input to the inspection apparatus 100 after conversion into format data 203 unique to the inspection apparatus in each layer. In this case, the format data 203 can be set to a data format that is unique to the inspection apparatus 100 or to the data format that is compatible with a drawing apparatus.

The format data 203 is input to the magnetic disk drive 109 in FIG. 1. That is, the design pattern data used during the formation of the pattern in the mask 101 is stored in the magnetic disk drive 109.

The figure patterns included in the design pattern may be a rectangle or a triangle as a basic graphic pattern. For example, Graphic data in which the shape, size, and position of each figure pattern is stored in the magnetic disk drive 109. For example, the graphic data is information such as a coordinate (x, y) from the original position of the graphic pattern, a side length, and a figure code that becomes an identifier identifying a figure pattern type such as a rectangle and a triangle.

A set of graphic patterns existing within a range of several tens of micrometers is generally called a cluster or a cell, and the data is layered using the cluster or cell. In the cluster or cell, a disposition coordinate and a repetitive amount are defined in the case that various graphic patterns are separately disposed or repetitively disposed with a certain distance. The cluster or cell data is disposed in a strip-shaped region called a stripe. The strip-shaped region has a width of several hundred micrometers and a length of about 100 mm that corresponds to a total length in an X-direction or a Y-direction of the mask 101.

The pattern generating circuit 111 reads the input design pattern data from the magnetic disk drive 109 through the control computer 110.

In the pattern generating circuit 111, the design pattern data is converted into image data (bit pattern data). That is, the pattern generating circuit 111 extracts the design pattern data to individual data of each graphic pattern, and interprets the figure pattern code and figure pattern dimension, which indicate the figure pattern shape of the design pattern data, The design pattern data is extracted to binary or multi-level image data as the pattern disposed in a square having a unit of a grid of a predetermined quantization dimension. Then an occupancy rate of the graphic pattern in the design pattern is calculated in each region (square) corresponding to a sensor pixel, and the occupancy rate of the graphic pattern in each pixel becomes a pixel value.

The image data converted by the pattern generating circuit 111 is transmitted to the reference image generating circuit 112, that is, the reference image producing unit, and used to produce a reference image (also referred to as reference data).

The optical image data 204 output from the sensor circuit 106 is transmitted to the comparison circuit 108 together with data indicating a position of the mask 101 on the XYθ-table 102. The data is output from the position measuring circuit 107. The reference image is also transmitted to the comparison circuit 108.

In the comparison circuit 108, the optical image data 204 and the reference data are compared to each other using a proper comparison determination algorithm. In the configuration of FIG. 1, transmission images are compared to each other. In a configuration in which a reflection optical system is used, reflection images are compared to each other, or a comparison determination algorithm in which transmission and reflection are combined is used. As a result of the comparison, in the case that a difference between the two exceeds a predetermined threshold, the position is determined to be the defect.

For example, the determination threshold registered as a line width defect is assigned by a line width dimension difference (nm) between the optical image data 204 and the reference data and a dimension ratio (%). For example, the determination thresholds of the line width dimension difference of 16 nm and the dimension ratio of 8% are assigned in two ways. When the dimension difference with the reference data is 20 nm while the pattern of the optical image data 204 has the line width of 200 nm, because the pattern is larger than both the thresholds of the dimension difference and dimension ratio, the pattern is registered as the defect.

In the case that the line width is larger than that of the reference data and the case that the line width is smaller than that of the reference data, the threshold of the defect determination may separately be assigned. The threshold may be assigned in both the case that not the line width but the inter-pattern distance is larger than that of the reference data and the case that the inter-pattern distance is smaller than that of the reference data. The thresholds of a hole diameter or a diameter dimension ratio may be assigned for the pattern having a hole shape. In this case, the threshold may be assigned for sections in the X-direction and Y-direction of the hole.

In the comparison circuit 108, the reference image corresponding to the (stripe-shaped) optical image data 204 is divided into small rectangular regions of several tens of micrometers called inspection frames. A sensor frame image extracted from the optical image data 204 and a reference frame image extracted from the reference image are input to a comparison unit. The comparison unit compares the sensor frame image and the reference frame image to each other to detect the defect. Several tens of comparison units are included in the comparison circuit 108 so as to concurrently process multiple inspection frames. Each comparison unit captures the unprocessed frame image when ending the processing of one inspection frame. Therefore, many inspection frames are sequentially processed.

The processing of the comparison unit is specifically performed as follows. The sensor frame image and the reference frame image are aligned with each other. At this point, in order to align edge positions of the pattern or luminance peak positions, the sensor frame image or the reference frame image is shifted in parallel in units of sensor pixels, and the sensor frame image and the reference frame image are aligned up to the sensor pixel or less by prorating luminance values of neighboring pixels. After the alignment, a level difference between the sensor frame image and the reference frame image is evaluated in each pixel, and derivative values of the pixels in a pattern edge direction are compared to each other, whereby the defect is detected according to the proper comparison algorithm. Hereinafter, occasionally the comparison of the sensor frame image and the reference frame image is simply referred to as comparison of the optical image and the reference image. The sensor frame images are compared to each other in the comparison by the die-to-die method. However, in this case, sometimes the comparison of the sensor frame images is simply referred to as the comparison of the optical images.

At the same time, in the comparison circuit 108, the repetitive pattern in the optical image data 204 is searched for and extracted within a proper dimensional range, and the cells are compared to each other. The repetitive pattern is searched for by a method for extracting a pattern feature from a repetitive disposition command of the graphic pattern or cell included in the layer structure of the design data and the acquired optical image data 204. For example, a subframe that becomes one unit of a predetermined repetitive pattern is defined in the inspection frame of the optical image. The subframes are compared to each other in one inspection frame, and the repetitive pattern is determined to have the defect when the difference exists between the patterns of the subframes.

In the first embodiment, the optical image data 204 is also transmitted to the dimension measuring circuit 125. In the dimension measuring circuit 125, for example, the line width of the line pattern written in the mask 101 is measured from the optical image data 204. The reference image generating circuit 112 transmits the reference data to the dimension measuring circuit 125, and the position measuring circuit 107 transmits the data indicating the position of the mask 101 on the XYθ-table 102 to the dimension measuring circuit 125. In the dimension measuring circuit 125, the line width of the pattern corresponding to the line pattern is measured from the reference data. The dimension difference or dimension ratio between the pattern line width of the optical image and the pattern line width of the reference image is obtained based on the measured value.

The pattern dimension measurement in the dimension measuring circuit 125 is performed concurrently with the acquisition of the optical image of the mask 101. Alternatively, for example, the pattern dimension measurement in the dimension measuring circuit 125 may be performed concurrently with the inspection performed by the comparison circuit 108.

The dimension measuring circuit 125 is an example of the dimension difference/dimension ratio acquisition unit of the invention. In the embodiment, the space width between the line patterns, namely, the inter-line distance is measured instead of the line width, and the difference or ratio between the inter-line distances may be obtained. Both the dimension difference and the dimension ratio between the line widths or the inter-line distances may be obtained.

In the dimension difference or the dimension ratio, for example, the pattern in the mask 101 is divided to form multiple inspection regions, and the line width of each pixel is obtained for the optical image of each inspection region. Then, a frequency of the obtained line width is compiled, and an average value of the line widths is calculated from the compiled result of the frequency distribution. The dimension difference or dimension ratio of the line width is obtained from the average value and the line width obtained from the reference image. Specifically, the method disclosed in Japanese patent No. 3824542 can be applied.

The data of the dimension difference or dimension ratio, which is obtained by the dimension measuring circuit 125, is transmitted to the map producing circuit 126, that is, the dimension distribution acquisition unit. In the map producing circuit 126, for example, a map of the dimension difference or dimension ratio of the pattern line width in the surface on the mask 101 is produced based on the transmitted data. The produced map is stored in the magnetic disk drive 109. The inspection apparatus 100 does not necessarily include the map producing circuit 126, but the dimension measuring circuit 125 may have the map producing function, or the map may be produced by an external computer. Alternatively, a defect determination may be made by the data of the dimension difference or dimension ratio, which is obtained by the dimension measuring circuit 125, without producing the map.

When the comparison circuit 108 determines that the pattern has a defect, the coordinate of the defect and the optical image and reference image, which are the basis of the defect determination, are stored as a mask inspection result 205 in the magnetic disk drive 109. The mask inspection result 205 is transmitted to a review tool 500 as illustrated in FIG. 2. A review process is an operation in which the operator determines whether the detected defect will become a practical problem. For example, the operator visually determines whether the defect needs to be corrected by comparing the reference image that is the basis of the defect determination to the optical image including the defect.

The defect information determined through the review process is also stored in the magnetic disk drive 109 of FIG. 1. As illustrated in FIG. 2, when the defect to be corrected is confirmed by the review tool 500, the mask 101 is transmitted to a repair apparatus 600, that is, the external device of the inspection apparatus 100 together with a defect information list 207. Because a correction method depends on whether the defect is projected or recessed, a defect type including the distinction between the projection and the recess and the defect coordinate are added to the defect information list 207.

An example of a method for inspecting the mask 101 with the inspection apparatus 100 in FIG. 1 will be described below.

Figure 4:
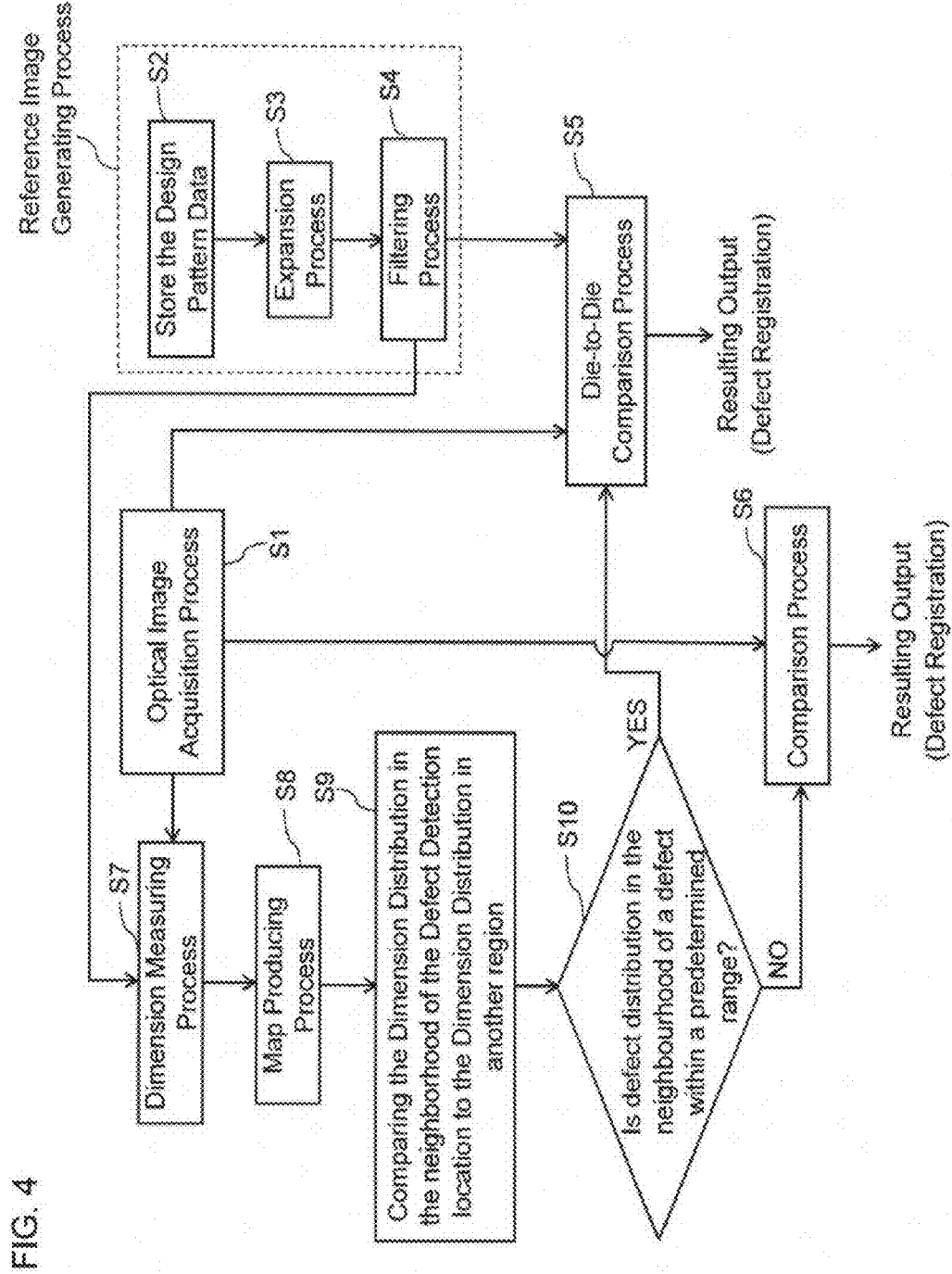
FIG. 4 is a flowchart illustrating an example of the inspection method according to the first embodiment.

FIG. 4 is a flowchart illustrating an example of the inspection method of the first embodiment. As illustrated in FIG. 4, an inspection process includes a process of acquiring the optical image of the mask 101 (optical image acquisition process; S1), a process of storing the design pattern data of the pattern formed in the mask 101 (Store the Design Pattern data; S2), an pattern generating process (S3) and a filtering process (S4), that is, an example of the process of generating the reference image (S3), a process of comparing the optical image to the image that becomes a reference (comparison process; S5 and S6), a process of measuring the pattern dimension difference from the optical image and the reference image (dimension measuring process; S7), a process of producing the dimension difference map in the surface of the mask 101 based on the measured dimension difference (map producing process; S8), a process of comparing the dimension distribution in the neighborhood of the defect detection position to the dimension distribution in another region (S9), and a process of determining whether the dimension distribution in the neighborhood of the defect detection position falls within a predetermined range (S10).

(Optical Image Acquisition Process)

The mask 101 is positioned on the XYθ-table 102. In order to obtain the correct inspection result, it is necessary to locate the mask 101 at a predetermined position of the XYθ-table 102. Therefore, an alignment mark is usually formed in the mask 101, and the mask 101 is aligned on the XYθ-table 102 using the alignment mark.

Figure 11:
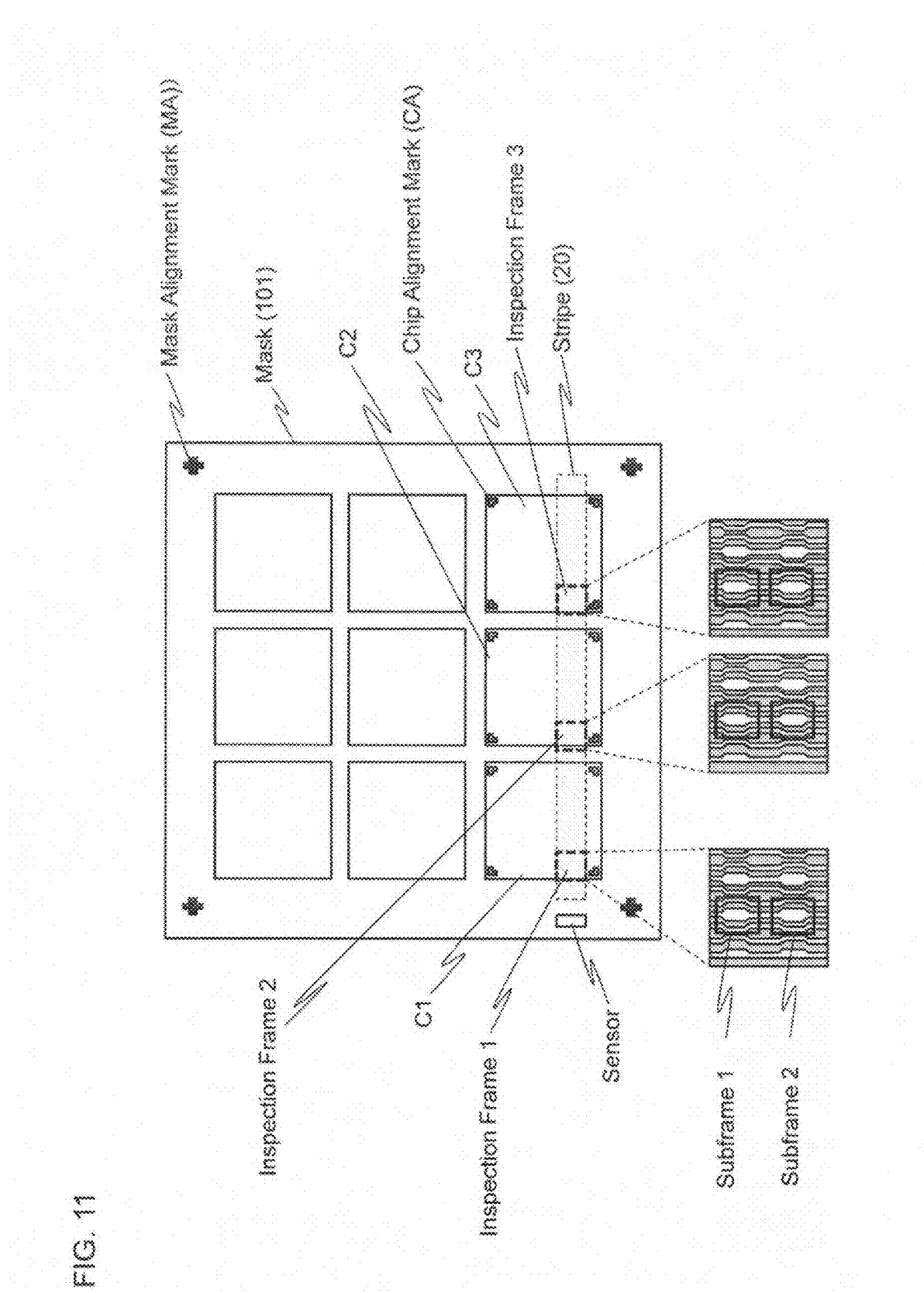
FIG. 11 is another example of a schematic diagram of a chip pattern of a mask.

The alignment of the mask 101 (plate alignment) will be described with reference to FIG. 11. In the example of FIG. 11, cross mask alignment marks MA are formed at four corners of the mask 101. Multiple chip patterns (C1, C2, C3, . . . ) are formed in the mask 101, and chip alignment marks CA are also formed in each chip. The mask 101 is positioned on the XYθ-table 102, and it is assumed that the XYθ-table 102 includes an XY-stage moving in a horizontal direction and a θ-stage that is disposed on the XY-stage to move in a rotational direction.

Specifically, in the alignment process, an X-axis and a Y-axis of the pattern, that is, the inspection target are aligned with running axes of the XY-stage while the mask 101 is positioned on the XYθ-table 102.

In the mask alignment marks MA provided in the four positions, the images of the two mask alignment marks MA having the smaller values of the Y-coordinates are captured, the θ-stage is rotated such that the two mask alignment marks MA correctly become the equal Y-coordinate, thereby finely adjusting the rotation direction of the mask 101. At this point, the distance between the mask alignment marks MA is correctly measured. Then the images of the two mask alignment marks MA having the larger values of the Y-coordinates are captured. Therefore, the coordinates of the mask alignment marks MA at four positions are correctly measured.

It is discovered from the above measurement that the two mask alignment marks MA having the larger values of the Y-coordinates are located at vertices of a trapezoid having the two mask alignment marks MA having the smaller values of the Y-coordinates at both ends of a base. At this point, because the mask 101 originally has the rectangular shape, the two mask alignment marks MA having the larger values of the Y-coordinates are supposed to be located at the vertices of the rectangle. However, the measurement result shows that the two mask alignment marks MA having the larger values of the Y-coordinates are located at the vertices of the trapezoid. In consideration of these facts, it is discovered the shape of the mask 101 is deformed. Accordingly, it is assumed that the region of the pattern that becomes the inspection target has the trapezoidal deformation similar to the trapezoid and expansion and contraction of the distance between the mask alignment marks MA, and compensation is performed on the assumption of the trapezoidal deformation and the expansion and contraction of the distance when the reference image generating circuit 112 generates the reference data.

The mask alignment mark MA is not necessarily provided in the mask 101. In this case, the alignment is performed using the vertex of the corner or the side of the edge pattern, which is close to an outer periphery of the mask 101 and equal to the coordinates of the XY-coordinate, in the pattern that becomes the inspection target.

Figure 3:
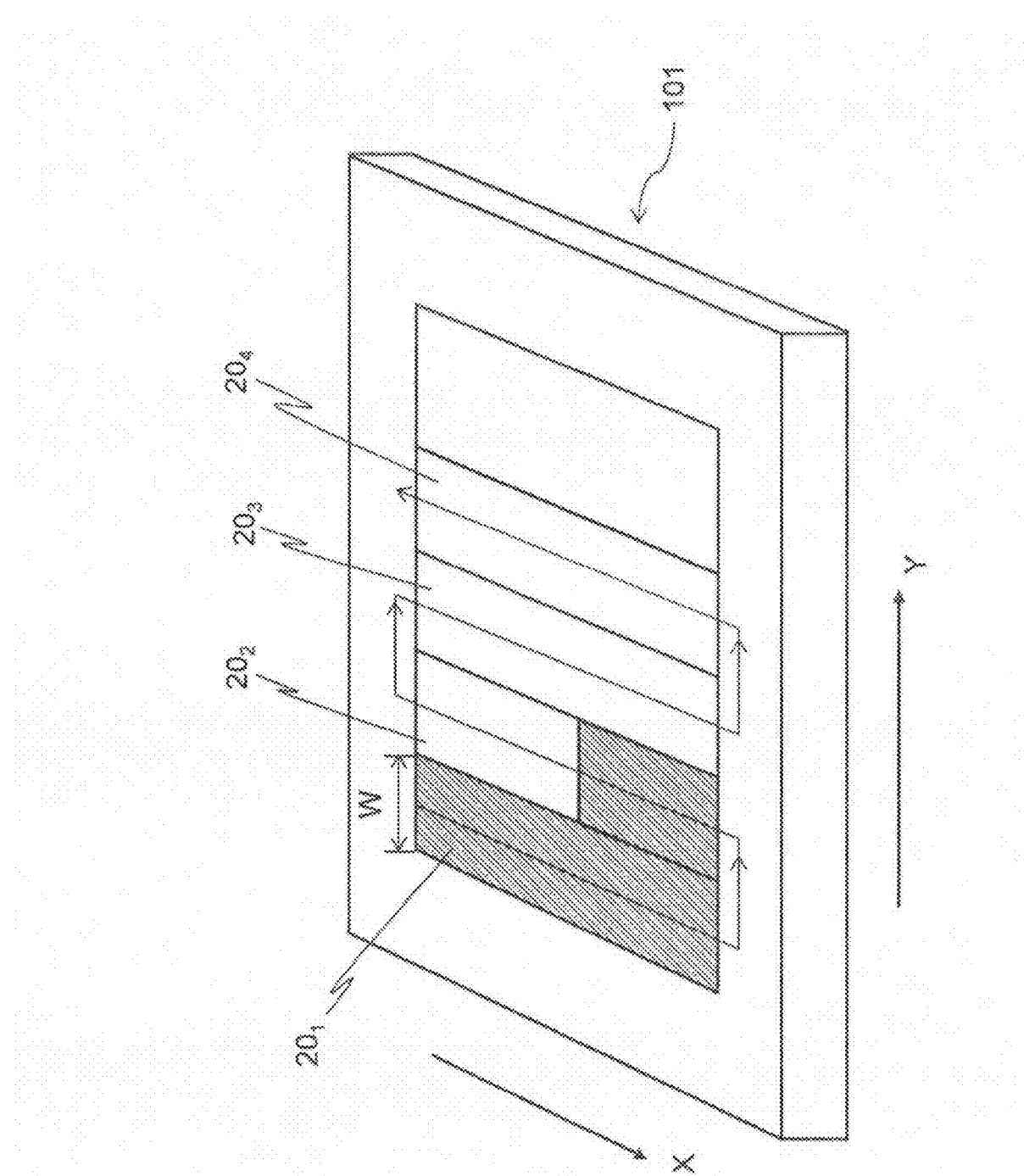
FIG. 3 is a view illustrating a procedure for acquiring an optical image for the detection of the defect of the pattern formed in the mask.

In the optical image acquisition process of the first embodiment, the configuration unit A in FIG. 1 acquires the optical image of the mask 101. FIG. 3 is a view illustrating an optical image acquiring procedure for the purpose of the detection of the defect of the pattern formed in the mask 101. As described above, the optical image corresponds to the optical image data 204 in FIG. 2.

In FIG. 3, it is assumed that the mask 101 is positioned on the XYθ-table 102 in FIG. 1. The inspection region in the mask 101 is virtually divided into the strip-shaped multiple inspection regions, namely, stripes $20_1$, $20_2$, $20_3$, $20_4$, . . . as illustrated in FIG. 3. For example, each stripe is a region having the width of several hundred micrometers and the length of about 100 mm corresponding to the total length in the X-direction or Y-direction of the mask 101.

The optical image is acquired in each stripe. That is, in acquiring the optical image in FIG. 3, the operation of the XYθ-table 102 is controlled such that the each stripe $20_1$, $20_2$, $20_3$, $20_4$, . . . is continuously scanned. Specifically, the optical image of the mask 101 is acquired while the XYθ-table 102 moved in the −X-direction of FIG. 3. The image having a scan width W in FIG. 3 is continuously input to the photodiode array 105 in FIG. 1. That is, the image of the second stripe $20_2$ is acquired after the image of the first stripe $20_1$ is acquired. In this case, after the XYθ-table 102 moves in the −Y-direction in a stepwise manner, the optical image is acquired while the XYθ-table 102 moves in the direction (X-direction) opposite to the direction (−X-direction) in which the image of the first stripe $20_1$ is acquired, and the image having the scan width W is continuously input to the photodiode array 105. In the case that the image of the third stripe $20_3$ is acquired, after moving in the −Y-direction in the stepwise manner, the XYθ-table 102 moves in the direction opposite to the direction (X-direction) in which the image of the second stripe $20_2$ is acquired, namely, the direction (−X-direction) in which the image of the first stripe $20_1$ is acquired. An arrow in FIG. 3 indicates the optical image acquiring direction and sequence, and a hatched portion indicates the region where the optical image is already acquired.

FIG. 10 illustrates a state in which the optical image is being acquired. In FIG. 10, $2n$ chip patterns are formed in a predetermined region in the mask 101, and a cell A and a cell B each of which includes the repetitive pattern are formed in each chip pattern. The sensor captures the image of the pattern along the stripe in the order of the first chip, the second chip, the third chip, . . . , and n-th chip.

The photodiode array 105 performs the photoelectric conversion to the pattern image formed on the photodiode array 105 in FIG. 1, and the sensor circuit 106 performs the A/D (analog-digital) conversion to the pattern image. Then the optical image is transmitted from the sensor circuit 106 to the comparison circuit 108 in FIG. 1.

The A/D-converted sensor data is input to a digital amplifier (not illustrated) that can adjust an offset and a gain in each pixel. The gain for each pixel of the digital amplifier is fixed in a calibration process. For example, in the calibration process for transmitted light, a black level is fixed while the image of a light-shielding region in the mask 101, sufficiently wide with respect to an area in which the image is captured by the sensor, is captured. Then a white level is fixed while the image of a transmitted light region in the mask 101, sufficiently wide with respect to an area in which the image is captured by the sensor, is captured. At this point, in consideration of a fluctuation in light quantity during the inspection, the offset and the gain are adjusted in each pixel such that amplitudes of the white level and black level are distributed in a range of 10 to 240 corresponding to about 4 to about 94% of 8-bit gradation data.

(Storage Process)

In the case of inspection by the die-to-database comparison method, the reference image generated from the design pattern data becomes a reference of the defect determination. In the inspection apparatus 100, the design pattern data used to form the pattern in the mask 101 is stored in the magnetic disk drive 109.

(Pattern Generating Process)

In the pattern generating process, the pattern generating circuit 111 in FIG. 1 reads the design pattern data from the magnetic disk drive 109 through the control computer 110, and converts the read design pattern data of the mask 101 into the binary or multi-value image data (design image data). The image data is transmitted to the reference image generating circuit 112.

(Filtering Process)

In the filtering process, the reference image generating circuit 112 in FIG. 1 performs the proper filtering to the design pattern data, that is, the graphic image data. The reason is as follows.

In the production process because roundness of the corner and a finished dimension of the line width is adjusted, the pattern in the mask 101 is not strictly matched with the design pattern. The optical image data 204, that is, the optical image obtained from the sensor circuit 106 in FIG. 1 is faint due to a resolution characteristic of the magnifying optical system 104 or an aperture effect of the photodiode array 105, in other words, the state in which a spatial lowpass filter functions.

Therefore, the mask that becomes the inspection target is observed in advance of the inspection, a filter coefficient imitating the production process or a change of an optical system of the inspection apparatus is determined to subject the design pattern data to a two-dimensional digital filter. Thus, the processing of imitating the optical image is performed to the reference image.

The learning process of the filter coefficient may be performed using the pattern of the mask that becomes the reference fixed in the production process or a part of the pattern of the mask (in the first embodiment, mask 101) that becomes the inspection target. In the latter case, the filter coefficient is acquired in consideration of the pattern line width of the region used in the learning process or a finished degree of the roundness of the corner, and reflected in a defect determination criterion of the whole mask.

In the case that the mask that becomes the inspection target is used, advantageously the learning process of the filter coefficient can be performed without removing influences such as a variation of production lot and a fluctuation in condition of the inspection apparatus. However, when the dimension fluctuates in the surface of the mask, the filter coefficient becomes optimum with respect to the position used in the learning process, but the filter coefficient does not necessarily become optimum with respect to other positions, which results in a pseudo defect. Therefore, preferably the learning process is performed around the center of surface of the mask that is hardly influenced by the fluctuation in dimension. Alternatively, the learning process is performed at multiple positions in the surface of the mask, and the average value of the obtained multiple filter coefficients may be used.

(Dimension Measuring Process)

In the dimension measuring process, the pattern dimension difference is measured from the optical image and the reference image. In the inspection apparatus 100 in FIG. 1, the dimension measuring circuit 125 measures the dimension difference of the pattern line width between the optical image and the reference image using the optical image data 204 output from the sensor circuit 106 and the reference data output from the reference image generating circuit 112. The dimension ratio of the pattern line width may be measured instead of or in addition to the dimension difference of the pattern line width, or the inter-pattern distance difference or the inter-pattern distance ratio may be obtained instead of or in addition to the pattern line width.

For example, a frequency at which the dimension measuring circuit 125 measures the dimension difference during the inspection can be set to the proper number of sampling times (about 1000 points) in the length direction (X-direction) of the stripe ($20_1$, $20_2$, $20_3$, $20_4$, . . . ) in FIG. 3, and set to almost the same number of sampling times in the width direction (Y-direction) of the stripe. A proper line pattern in which a distance of an edge pair can be measured is used in the neighborhood of a potential point where the dimension difference is measured. In this case, the one edge pair may be used. However, preferably the dimension difference is measured using the edge pairs of multiple positions, the frequency of the obtained value is compiled, and the highest frequency value (mode) of the compiled result of the frequency distribution is used as a representative value. In the case that the edge pair is not found in the neighborhood of the potential point, or in the case of a small number of edge pairs, the dimension difference does not need to be measured, or the mode may be obtained from the limited number of samples.

(Map Producing Process)

In the inspection apparatus 100, at the same time as the optical image of the mask 101 is acquired, the dimension measuring circuit 125 measures the pattern dimension difference between the optical image and the reference image, and the obtained data of the dimension difference is transmitted to the map producing circuit 126. In the map producing circuit 126, the map expressing the dimension distribution in the surface of the mask is produced from the accumulated data of the dimension difference. The dimension distribution in the currently inspected stripe or the dimension distribution of the stripe in which the inspection is already performed in the same mask can be recognized from the map.

(Die-to-Database Comparison Process and Cell Comparison Process)

As illustrated in FIG. 2, the optical image data 204 acquired in the optical image acquisition process is transmitted to the comparison circuit 108. The reference image generating circuit 112 transmits the reference data to the comparison circuit 108. The comparison circuit 108 includes the first comparator 108a and the second comparator 108b, and the first comparator 108a compares the optical image data 204 to the reference data by the die-to-database method.

Concurrently with the processing performed by the die-to-database comparison method, the second comparator 108b searches the repetitive pattern in the optical image data 204, and extracts the repetitive pattern in a proper dimension range to perform the cell comparison. However, in the case that the cell that becomes the reference does not exist because the repetitive pattern does not exist near the cell that becomes the inspection target, the processing is performed only by the die-to-database comparison method.

In both methods, the data that becomes the inspection target and the data that becomes the reference of the defect determination are compared to each other using the proper comparison determination algorithm. The data that becomes the inspection target is determined to be the defect in the case that the difference between the two exceeds the predetermined threshold.

For example, it is assumed that the chip patterns are matrix aligned in the mask 101. In the die-to-database comparison method, when the n-th chip is considered as the inspection target, the n-th chip is determined to be the defect in the case that the pattern difference between the optical image and reference image of the n-th chip exceeds the predetermined threshold. On the other hand, in the cell comparison method, the patterns that are separated from each other by a pitch of the repetitive pattern (cell) such as the memory mat portion in the one chip are compared to each other, and the pattern is determined to be the defect in the case that the difference between the two exceeds the predetermined threshold. In this case, when the specific cell in the n-th chip is the inspection target, the optical image preceding the specific cell becomes the reference image to be compared. For example, assuming that the second cell is the inspection target in the cell A of FIG. 10, the optical image of the first cell becomes the reference image.

More specifically the defect determination can be made by the following two methods. One of the methods is the method for determining that the inspection target is the defect in the case that the difference exceeding a predetermined threshold is recognized between the position of a contour in the reference image and the position of a contour in the optical image. The other method is the method for determining that the inspection target is the defect in the case that the ratio of the pattern line width in the reference image and the pattern line width in the optical image exceeds a predetermined threshold. In this method, the ratio of the inter-pattern distance in the reference image and the inter-pattern distance in the optical image may be used.

(Process of Determining Whether Dimension Distribution in the Neighborhood of the Defect Detection Position Falls within Predetermined Range by Comparing Dimension Distribution in Neighborhood of Defect Detection Position to Dimension Distribution of Another Region)

In the case that the dimension measuring circuit 125 measures the pattern dimension concurrently with the acquisition of the optical image of the mask 101, the latest data is referred to in the dimension difference data measured by the dimension measuring circuit 125 when the defect is detected by the die-to-database comparison method. When the dimension distribution from the position where the defect is detected to the preceding position where the dimension difference is obtained falls within the predetermined range by comparing the dimension distribution to the dimension distribution in the chip and the dimension distribution among the chips, the result of the die-to-database comparison method, namely, the defect coordinate and the optical image and reference image, which are the basis of the defect determination are stored as the mask inspection result 205 in the magnetic disk drive 109.

In the case that the dimension measuring circuit 125 measures the pattern dimension concurrently with the inspection of the comparison circuit 108, at a time point when the defect is detected by the die-to-database comparison method, the dimension of the pattern in which the comparison is already performed is measured, however the dimension of the pattern in which the comparison is not performed is not measured. Therefore, in this case, the latest data is referred to from the dimension difference data measured by the dimension measuring circuit 125.

On the other hand, the defect is detected by the die-to-database comparison method, and the dimension distribution from the position where the defect is detected to the preceding position where the dimension difference is obtained exceeds the predetermined range by comparing the dimension distribution to the dimension distribution in the chip and the dimension distribution among the chips. In this case, the result of the die-to-database comparison method is not adopted with respect to the position, but the result of the cell comparison method performed concurrently is adopted. At this point, whether the defect is detected as a result of the cell comparison method not a problem. That is, even the position determined to be the defect by the die-to-database comparison method is not registered as the defect unless the position is determined to be the defect by the cell comparison method.

However, in the case that the cell that becomes the reference does not exist because the repetitive pattern does not exist near the cell that becomes the inspection target, the processing is performed only by the die-to-database comparison method. In this case, even if the dimension distribution from the position where the defect is detected to the preceding position where the dimension difference is obtained exceeds the predetermined range by comparing the dimension distribution to the dimension distribution in the chip and the dimension distribution among the chips, preferably the result of the die-to-database comparison method is adopted. That is, the coordinate of the defect detected by the die-to-database comparison method and the optical image and reference image, which are the basis of the defect determination, are stored as the mask inspection result 205 in the magnetic disk drive 109.

By way of example, the dimension distribution from the position where the defect is detected to the preceding position where the dimension difference is obtained is compared to the dimension distribution in the chip and the dimension distribution among the chips. Alternatively, the dimension distribution from the position where the defect is detected to the preceding position where the dimension difference is obtained may be compared to the dimension distribution of the region separated by the chip pitch.

For example, when the dimension distribution from the position where the defect is detected to the preceding position where the dimension difference is obtained falls within the predetermined range by comparing the dimension distribution to (1) the dimension distribution in the stripe including the position determined to be the defect or (2) the dimension distribution of the chip pattern assumed from the stripe in which the dimension difference is acquired in advance of the stripe including the position determined to be the defect, the defect coordinate and the optical image and reference image, which are the basis of the defect determination may be stored in the magnetic disk drive 109. At this point, (1) the dimension distribution and (2) the dimension distribution are derived from the map produced by the map producing circuit 126. (1) The dimension distribution and (2) the dimension distribution can also directly be derived from the dimension difference data obtained by the dimension measuring circuit 125.

In the above modification, the defect is detected by the die-to-database comparison method, and the dimension distribution from the position where the defect is detected to the preceding position where the dimension difference is obtained is compared to (1) the dimension distribution and (2) the dimension distribution. When the dimension distribution from the position where the defect is detected to the preceding position where the dimension difference is obtained deviates from the predetermined range, the result of the die-to-database comparison method is not adopted with respect to the position, but the result of the cell comparison method performed in parallel is adopted. In this case, whether the defect is detected as a result of the cell comparison method is not a problem. That is, even the position determined to be the defect by the die-to-database comparison method is not registered as the defect unless the position is determined to be the defect by the cell comparison method.

However, in the case that the cell that becomes the reference does not exist because the repetitive pattern does not exist near the cell that becomes the inspection target, the processing is performed only by the die-to-database comparison method. In this case, even if the dimension distribution from the position where the defect is detected to the preceding position where the dimension difference is obtained deviates from the predetermined range by comparing the dimension distribution to (1) the dimension distribution and (2) the dimension distribution, the result of the die-to-database comparison method is adopted. That is, the coordinate of the defect detected by the die-to-database comparison method and the optical image and reference image, which are the basis of the defect determination, are stored as the mask inspection result 205 in the magnetic disk drive 109.

In the case that the defect is detected by the die-to-database comparison method, the excess of the dimension distribution from the position where the defect is detected to the preceding position where the dimension difference is obtained over the predetermined range by comparing the dimension distribution in the chip and the dimension distribution among the chips means that the tendency of the line width in the region where the learning process of the two-dimensional digital filter is performed differs from the tendency of the line width in the position where the defect is detected during the generation of the reference data. The same holds true for the case that the dimension distribution from the position where the defect is detected to the preceding position where the dimension difference is obtained exceeds the predetermined range by comparing the dimension distribution to (1) the dimension distribution in the stripe including the position determined to be the defect or (2) the dimension distribution of the chip pattern assumed from the stripe in which the dimension difference is acquired in advance including the position determined to be the defect.

Therefore, in the first embodiment, whether the reference data is suitable for the reference of the defect determination by comparing the tendency of the dimension difference in the chip, the tendency of the dimension among the chips, the tendency of the dimension difference in the same chip, or the tendency of the dimension difference in the surface on the mask to the tendency of the dimension distribution from the position where the defect is detected to the preceding position where the dimension difference is obtained, can be determined. The determination can be made by the control computer 110 in FIG. 1. The control computer 110 determines whether the result of the cell comparison method exists, and the control computer 110 sets the result of the die-to-database comparison method to the mask inspection result 205 irrespective of the comparison result in the case that not the result of the cell comparison method but only the result of the die-to-database comparison method exists.

In the case that the dimension distribution from the position where the defect is detected to the preceding position where the dimension difference is obtained exceeds the predetermined range as a result of the comparison, because the dimension fluctuates in the surface of the mask, the filter coefficient of the defect detection position is not the optimum value, and the reference data is determined not to be suitable for the reference of the defect determination. The result of the cell comparison method is adopted. When the position is also determined to be the defect by the cell comparison method, the position is registered as the defect. For example, the control computer 110 stores the defect coordinate and the optical image and reference image, which are the basis of the defect determination, as the mask inspection result 205 in the magnetic disk drive 109. Unless the position is determined to be the defect by the cell comparison method, it is assumed that the defect detected by the die-to-database comparison method fails within an acceptable range, but the position is not registered as the defect. However, the result of the die-to-database comparison method may be stored.

When the dimension difference obtained by the dimension measuring circuit 125 is large, the position can be registered as the defect even if the position is not determined to be the defect in the comparison circuit 108. Therefore, in first embodiment, the defect determination can be made as follows.

For example, it is assumed that the threshold by which the comparison circuit 108 determines the line width defect is set to the line width dimension difference of 16 nm and the dimension ratio of 8%. The threshold of the defect determination for the measurement result of the dimension measuring circuit 125 is slightly relaxed compared with the threshold by which the comparison circuit 108 determines the line width defect, the line width dimension difference is set to 20 nm, and the dimension ratio is set to 10%. As to the predetermined range that becomes the criterion to which one of the result of the die-to-database comparison method and the result of the cell comparison method is adopted, the line width dimension difference is set to 12 nm or more, and the dimension ratio is set to 6% or more.

The result of the die-to-database comparison method is adopted, when the dimension difference obtained by the dimension measuring circuit 125 is less than 12 nm while the dimension ratio is less than 6%. On the other hand, the result of the cell comparison method is adopted, when the dimension difference obtained by the dimension measuring circuit 125 is greater than or equal to 12 nm and less than 20 nm while the dimension ratio is greater than or equal to 6% and less than 10%. The position is registered as the defect, when the dimension difference obtained by the dimension measuring circuit 125 is greater than or equal to 20 nm while the dimension ratio is greater than or equal to 10%.

The predetermined range that becomes the criterion to which one of the result of the die-to-database comparison method and the result of the cell comparison method is adopted is set in each mask that becomes the inspection target. At this point, the predetermined range is set to the range that does not exceed the threshold in the case that the position is determined to be the defect from the measured value of the dimension measuring circuit 125. The setting method is similar to the threshold setting method in the comparison circuit 108. That is, the predetermined range can individually be assigned for the case that the line width is larger than the reference data and the case that the line width is smaller than the reference data, and the predetermined range may be assigned for the case that not the line width but the inter-pattern distance is larger than the reference data and the case that the inter-pattern distance is smaller than the reference data. Additionally, the predetermined range of the hole diameter or the dimension ratio of the diameters can be assigned for the pattern having the hole shape. In this case, the predetermined range can be assigned for both the sections in the X-direction and Y-direction of the hole.

In the conventional inspection method, all the information on the defect detected by the die-to-database comparison method is registered. Therefore, sometimes the defect information that originally is not required to be detected is registered. On the other hand, in the first embodiment, the result of the die-to-database comparison method is replaced with the result of the cell comparison method in some cases in order to remove the influence of the line width distribution in the surface of the mask from the acquired data. Therefore, because the defect that originally needs not to be detected is removed from the mask inspection result, the number of defects that is reviewed by the operator decreases thus shortening the inspection time. Because the number of defects described in the defect information list is also decreased, the production yield of the mask can be improved. Additionally, the shape defect and the defect caused by the fluctuation in local line width can be detected by removing the influence of the line width distribution in the surface of the mask.

The map produced by the map producing circuit 126 of the first embodiment can be used to transfer the pattern of the mask 101 to the wafer. For example, when the exposure apparatus that transfers the pattern of the mask 101 to the wafer can input irradiation energy (dose) as a map, the map produced by the map producing circuit 126 is input to the exposure apparatus, and converted into the map of the irradiation energy, which allows the line width to be homogeneously transferred to the wafer. For example, in the position where the dimension difference becomes negative in the mask 101, namely, the position where the line width is thinned, the irradiation energy is adjusted such that the pattern transferred to the wafer is thickened. On the other hand, in the position where the dimension difference becomes positive in the mask 101, namely, the position where the line width is thickened, the irradiation energy is adjusted such that the pattern transferred to the wafer is thinned. Therefore, the line width of the pattern transferred to the wafer is homogenized evenly in the mask in which the pattern has the dimension distribution.

Second Embodiment

The inspection method in which the die-to-database comparison method and the cell comparison method are combined is described in the first embodiment. In a second embodiment, the inspection can be performed by the combination of the die-to-die comparison method and the cell comparison method. In this case, the inspection apparatus 100 in FIG. 1 may be used.

The die-to-die comparison method is the method for comparing the optical images of the same pattern in the chips of the different masks to each other in the case that the multiple chips partially or wholly having the pattern configuration are disposed in the same mask. That is, the chips repetitively formed in the mask are compared to each other in the die-to-die comparison method, and the repetitive patterns such as the memory mat portions in the one chip, namely, the cells are compared to each other in the cell comparison method. In the example of FIG. 10, the first chip and the second chip are compared to each other in the die-to-die comparison method. On the other hand, the first cell and second cell of the cell A are compared to each other in the cell comparison method.

The die-to-die comparison method and the cell comparison method will be described in detail with reference to FIG. 11. As illustrated in FIG. 11, the sensor captures the image of the pattern along the stripe 20 in the order of the chip C1, the chip C2, and the chip C3. In the comparison circuit 108, the captured image of the stripe data is divided in units of inspection frames, and an inspection frame 1 extracted from the chip C1 is compared to an inspection frame 2 extracted from the chip C2. The comparison is performed by the comparison unit, which is provided in the comparison circuit 108, to perform processing for each unit of the inspection frame.

Several tens of comparison units are provided so as to be able to concurrently process the multiple inspection frames, and each comparison unit captures the unprocessed frame image when ending the processing of one inspection frame. Specifically, the comparison unit aligns the image of the inspection frame 1 with the image of the inspection frame 2. At this point, in order to align the edge positions of the pattern or the luminance peak positions, the image of the inspection frame 1 or the image of the inspection frame 2 is shifted in parallel in units of sensor pixels. The image of the inspection frame 1 and the image of the inspection frame 2 are aligned up to the sensor pixel or less by prorating the luminance values of neighboring pixels. Then the first comparator 108a performs the die-to-die comparison to the image of the inspection frame 1 and the image of the inspection frame 2. Similarly, the die-to-die comparison is performed to the image of the inspection frame 2 and the image of the inspection frame 3.

As illustrated in FIG. 11, the subframe that becomes one unit of the repetitive pattern is defined in each inspection frame. For example, the second comparator 108b performs the cell comparison to the image of a subframe 1 and the image of a subframe 2 in the inspection frame 1.

In both the die-to-die comparison method and the cell comparison method, the level difference between the two images to be compared is evaluated in each pixel, and the derivative values of the pixels in the pattern edge direction are compared to each other, whereby the defect is detected according to the proper comparison algorithm.

Figure 5:
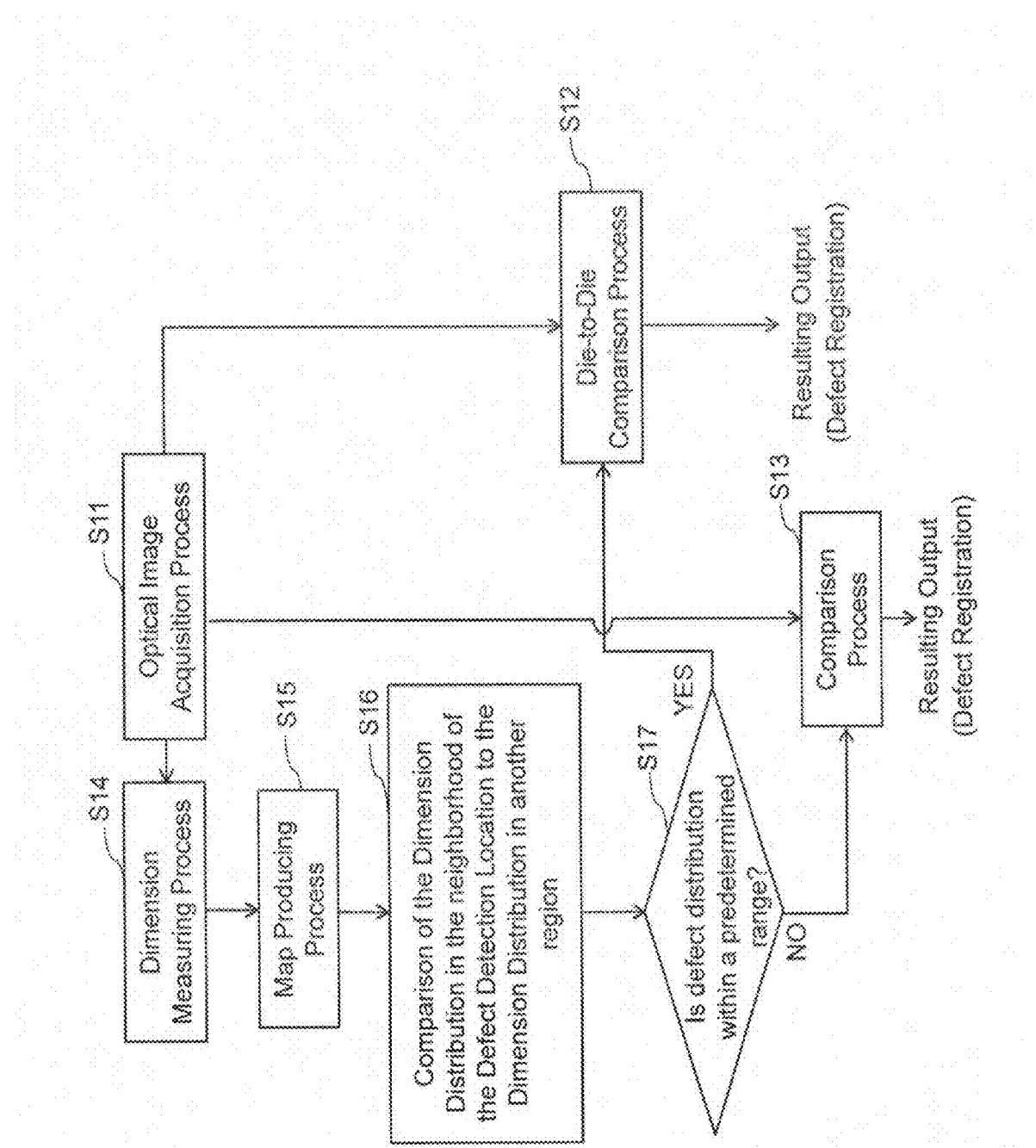
FIG. 5 is a flowchart illustrating an example of the inspection method according to the second embodiment.

FIG. 5 is a flowchart illustrating an example of the inspection method of the second embodiment. That is, FIG. 5 illustrates the inspection method in which the die-to-die comparison method and the cell comparison method are combined.

As illustrated in FIG. 5, the inspection process includes a process of acquiring the optical image of the mask 101 (optical image acquisition process; S11), a process of comparing the optical image that becomes the inspection target to the optical image (also referred to as a reference image) that becomes the reference (comparison process; S12 and S13), a process of measuring the pattern dimension difference from the optical image and the reference image (dimension measuring process; S14), a process of producing the dimension difference map in the surface of the mask 101 based on the measured dimension difference (map producing process; S15), a process of comparing the dimension distribution in the neighborhood of the defect detection position to the dimension distribution in another region (S16), and a process of determining whether the dimension distribution in the neighborhood of the defect detection position falls within a predetermined range (S17).

(Optical Image Acquisition Process)

Because the optical image acquisition process (S11) in FIG. 5 is already described in FIGS. 1 to 4 of the first embodiment, a description will be omitted.

(Dimension Measuring Process)

In the inspection apparatus 100, the dimension measuring circuit 125 measures the pattern dimension difference between the optical images in parallel with the acquisition of the optical image of the mask 101. In the dimension measuring process (S14), the pattern dimension difference between the optical image that becomes the inspection target and the optical image that becomes the reference is measured by the die-to-die comparison method. In the inspection apparatus 100 in FIG. 1, the dimension measuring circuit 125 measures the dimension difference of the pattern line width between the optical images using the optical image data output from the sensor circuit 106.

Figure 12:
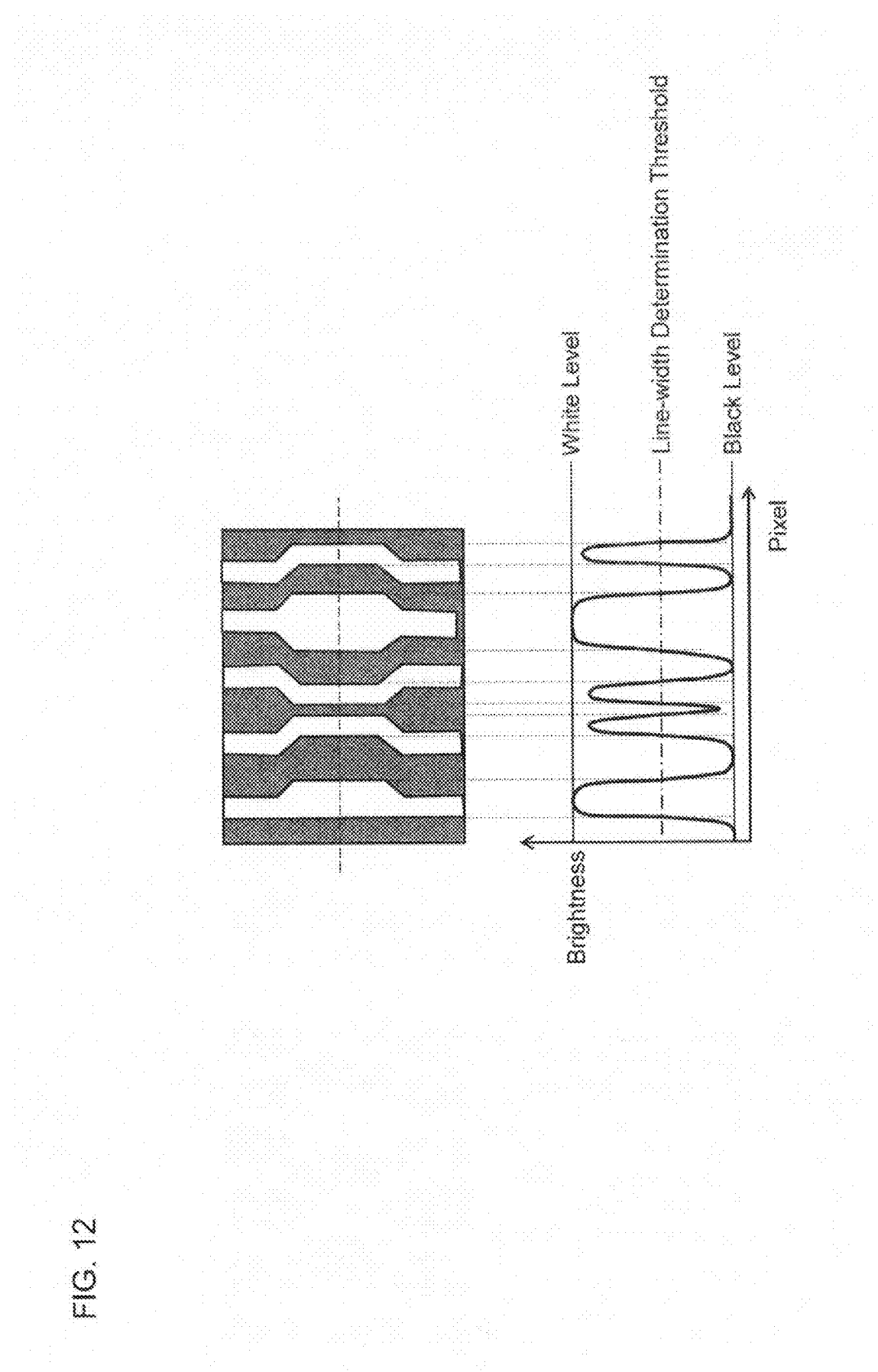
FIG. 12 is a view explaining a method for measuring a line width, and illustrates a schematic diagram of an optical image of a pattern formed in a mask and a luminance value of each pixel along a broken line.

A specific example of the line width measuring method will be described with reference to FIG. 12. FIG. 12 is a view schematically illustrating the optical image of the pattern formed in the mask 101 and a luminance value of each pixel along a broken line. For example, when the line and space pattern is inspected as illustrated in FIG. 12, the threshold in the middle of the white and black amplitude of the optical image is set to the threshold of the line width determination, and the position of the pattern edge is obtained from the pixel position where the luminance value of the optical image intersects the threshold. Then the positions of the pattern edges are converted into the distance of the edge pair to obtain the line width.

In the dimension measuring process, the positional information of the mask 101 on the XYθ-table 102 is added to the optical image data from the sensor circuit 106. The positional information is transmitted from the position measuring circuit 107. The dimension ratio of the pattern line width may be measured instead of or in addition to the dimension difference of the pattern line width, or the inter-pattern distance difference or the inter-pattern distance ratio may be obtained instead of or in addition to the pattern line width.

For example, the frequency at which the dimension measuring circuit 125 measures the dimension difference during the inspection can be set to the proper number of sampling times (about 1000 points) in the length direction (X-direction) of the stripe ($20_1$, $20_2$, $20_3$, $20_4$, . . . ) in FIG. 3, and set to approximately the same number of sampling times in the width direction (Y-direction) of the stripe. The proper line pattern in which the distance of the edge pair can be measured is used in the neighborhood of the potential point where the dimension difference is measured. In this case, the one edge pair may be used. However, preferably the dimension difference is measured using the edge pairs of multiple positions, the frequency of the obtained value is added, and the highest frequency value (mode) of the compiled result of the frequency distribution is used as a representative value. In the case that the edge pair is not found in the neighborhood of the potential point, or in the case of a small number of edge pairs, the dimension difference needs not to be measured, or the mode may be obtained from the limited number of samples.

(Map Producing Process)

The data of the dimension difference acquired by the dimension measuring circuit 125 is transmitted to the map producing circuit 126. In the map producing circuit 126, the map expressing the dimension distribution in the surface of the mask is produced from the accumulated data of the dimension difference (map producing process; S15). The dimension distribution in the currently inspected stripe or the dimension distribution of the stripe in which the inspection is already performed in the same mask can be recognized from the map.

(Die-to-Die Comparison Process and Cell Comparison Process)

The optical image data 204 acquired in the optical image acquisition process is transmitted to the comparison circuit 108 in FIG. 1. The comparison circuit 108 includes the first comparator 108*a* and the second comparator 108*b*. In the second embodiment, the first comparator 108*a* compares the optical image data to each other by the die-to-die method (die-to-die comparison process; S12). In parallel with the comparison performed by the die-to-die comparison method, the second comparator 108*b* searches the repetitive pattern in the optical image data 204, and extracts the repetitive pattern in the proper dimension range to perform the cell comparison (cell comparison process; S13). However, in the case that the cell that becomes the reference does not exist because the repetitive pattern does not exist near the cell that becomes the inspection target, the processing is performed only by the die-to-die comparison method.

In both the methods, the data that becomes the inspection target and the data that becomes the reference of the defect determination are compared to each other using the proper comparison determination algorithm. The data that becomes the inspection target is determined to be the defect in the case that the difference between the two exceeds the predetermined threshold.

For example, it is assumed that the lattice-shaped the chip patterns are matrix aligned in the mask 101. In the die-to-die comparison method, when the n-th chip is considered as the inspection target, the n-th chip is determined to be the defect in the case that the pattern difference between the optical image of the n-th chip and the optical image of the (n−1)-th chip exceeds the predetermined threshold. On the other hand, in the cell comparison method, the patterns that are separated from each other by the pitch of the repetitive pattern (cell) such as the memory mat portion in the one chip are compared to each other, and the pattern is determined to be the defect in the case that the difference between the two exceeds the predetermined threshold. In this case, when the specific cell in the n-th chip is the inspection target, the optical image preceding the specific cell becomes the reference image to be compared. For example, assuming that the second cell is the inspection target in the cell A of FIG. 10, the optical image of the first cell becomes the reference image.

For example, the determination threshold registered as the line width defect is assigned in units of line width dimension differences (nm) and units of dimension ratios (%). For example, the determination thresholds of the line width dimension difference of 16 nm and the dimension ratio of 8% are assigned in two ways. When the dimension difference with the reference data is 20 nm while the pattern of the optical image data 204 that becomes the inspection target has the line width of 200 nm, because the pattern is larger than both the thresholds of the dimension difference and dimension ratio, the pattern is registered as the defect.

The threshold of the defect determination may separately be assigned for the case that the line width is larger than that of the reference data and the case that the line width is smaller than that of the reference data. The threshold may be assigned in both the case that not the line width but the inter-pattern distance is larger than that of the reference data and the case that the inter-pattern distance is smaller than that of the reference data. The thresholds of the hole diameter and diameter dimension ratio may be assigned for the pattern having the hole shape. In this case, the threshold may be assigned for the sections in the X-direction and Y-direction of the hole.

When compared with the cell comparison method, basically the whole chips is set to the inspection range in the die-to-die comparison method, and the inspection can be performed irrespective of the portion in which the repetitive pattern exists. However, because the separation of the dies are larger than the distance between the cells that are compared to each other, the die-to-die comparison method is easily influenced by the dimension distribution in the surface of the mask. That is, when the chips in the regions having the different dimensions are compared to each other, the patterns having dimension biases (deviations) are compared to each other, which results in a problem in that the defect to be detected cannot be detected or the shape or line width which needs not to be detected is detected as the defect. Therefore, the result of the die-to-die comparison method is replaced with the result of the cell comparison method in some cases in order to remove the influence of the dimension distribution in the surface of the mask from the acquired data. A specific technique will be described below.

(Process of Determining Whether Dimension Distribution in the Surrounding Area of Defect Detection Position Falls within Predetermined Range by Comparing Dimension Distribution in Neighborhood of Defect Detection Position to Dimension Distribution of Another Region)

Figure 6:
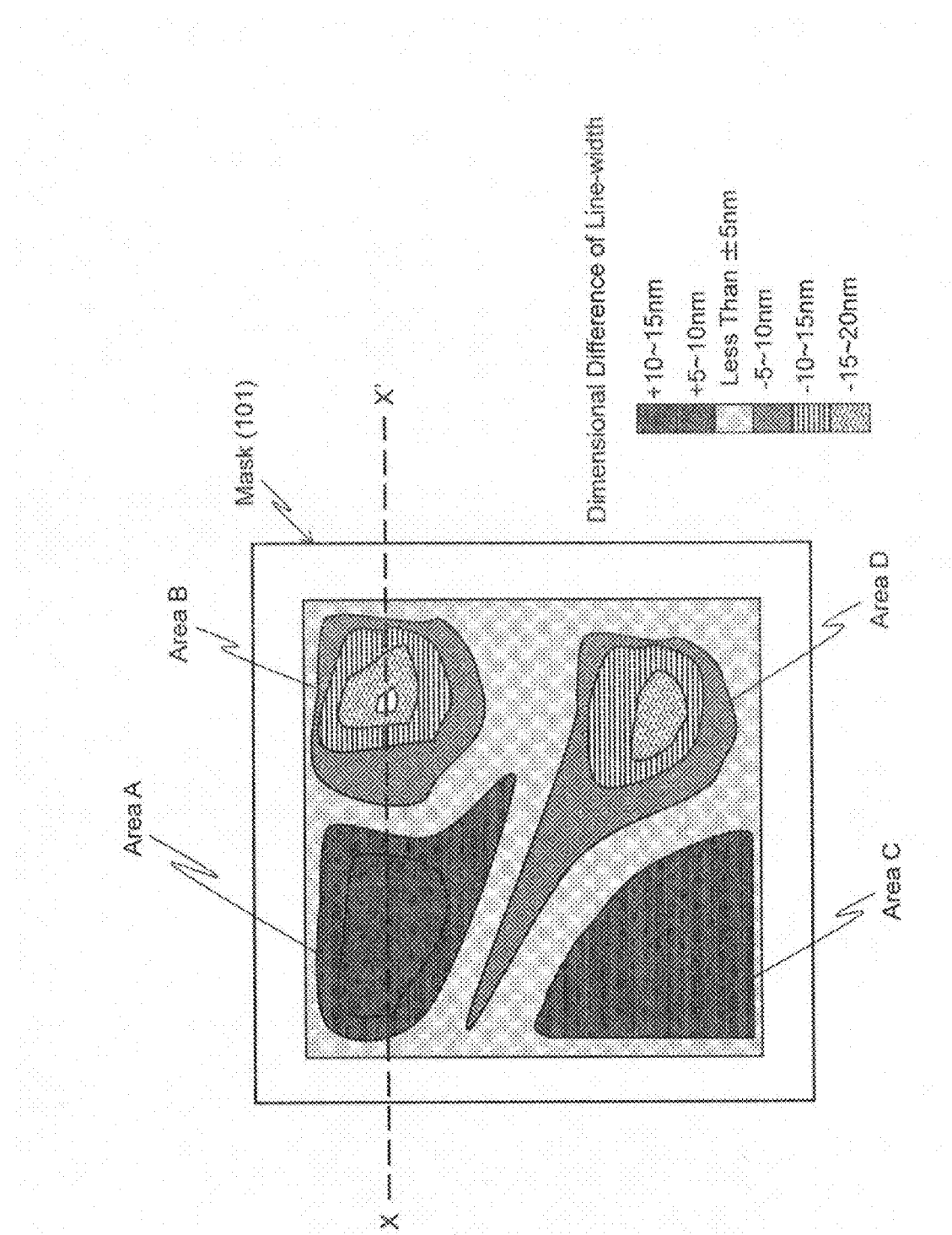
FIG. 6 illustrates an example of the dimension difference map of the mask.
Figure 7:
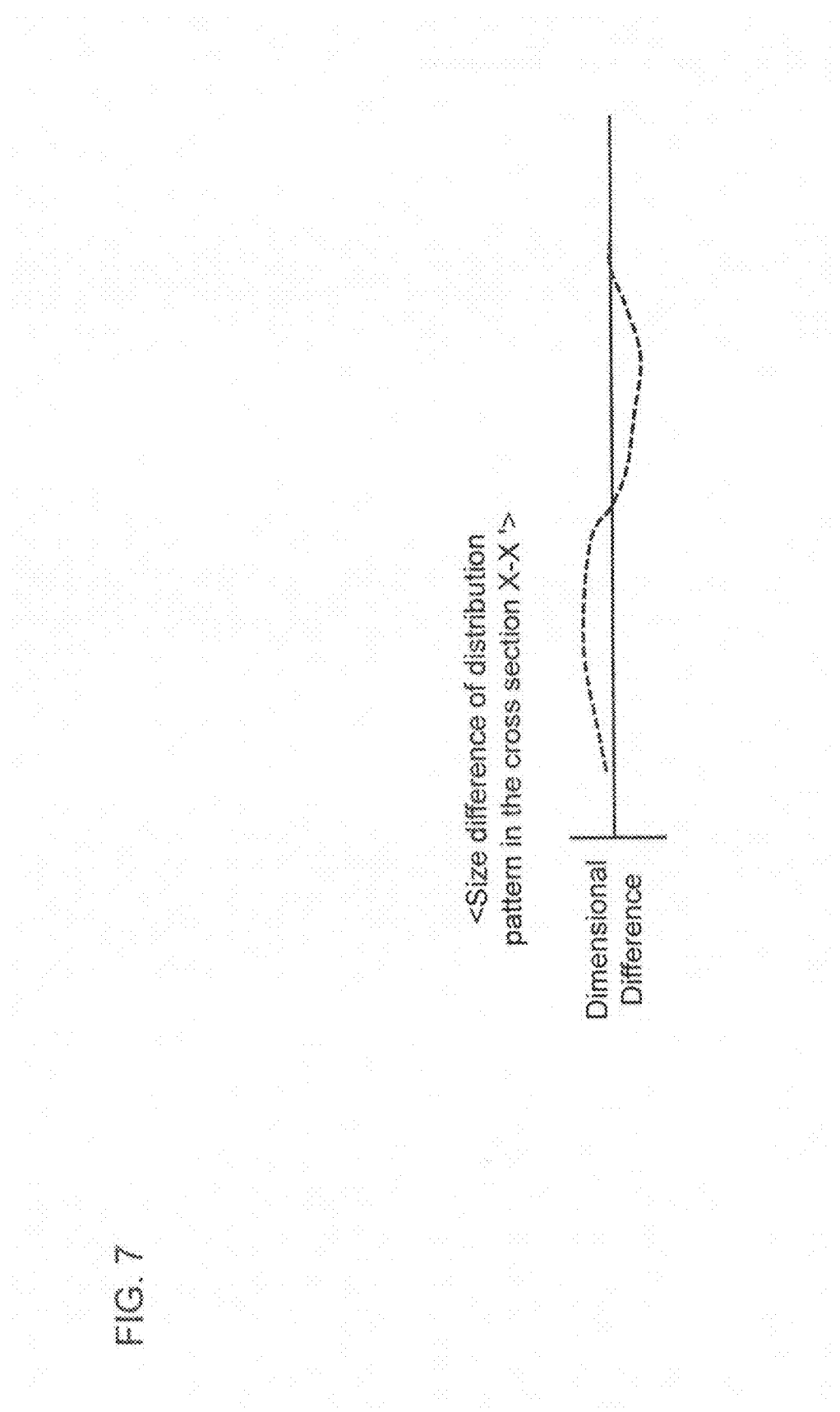
FIG. 7 illustrates the dimension distribution corresponding to the map in FIG. 6.
Figure 8:
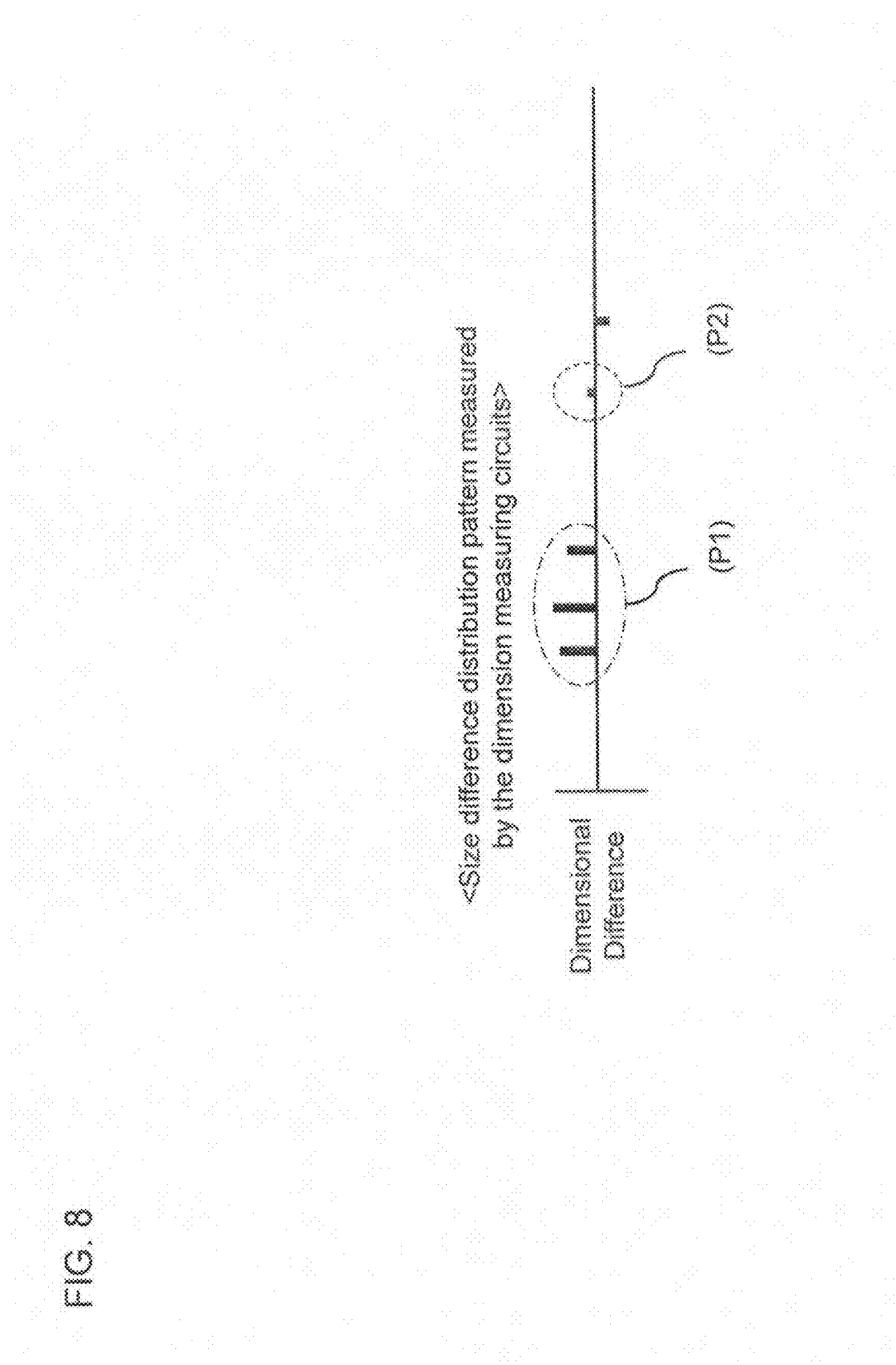
FIG. 8 illustrates the dimension distribution of the pattern measured by the dimension measuring circuit.
Figure 9:
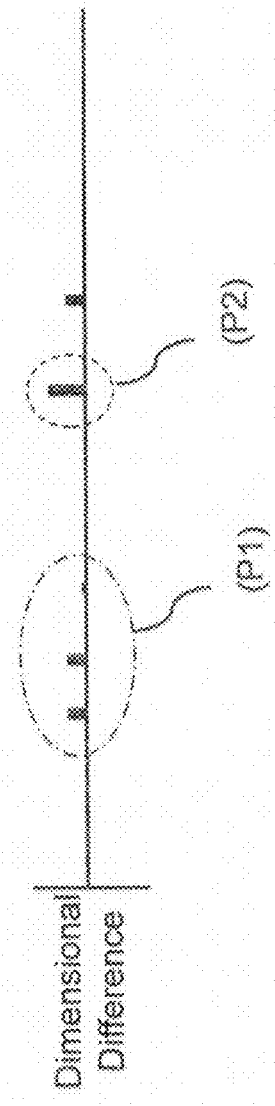
FIG. 9 illustrates the dimension difference from the reference value of the line width in the measured portion after the influence of the dimension distribution is removed.

FIG. 6 illustrates an example of the dimension difference map of the mask. In the example of FIG. 6, the line width is larger than the reference value in regions A and C. On the other hand, the line width is smaller than the reference value in regions B and D. FIGS. 7 to 9 are views illustrating the dimension distribution corresponding to the section along a line X-X' in FIG. 6. In FIGS. 7 to 9, a horizontal axis has the same scale, and an origin is positioned at the same position.

FIG. 7 illustrates the dimension distribution corresponding to the map in FIG. 6. FIG. 8 illustrates the dimension distribution of the pattern measured by the dimension measuring circuit. In FIG. 8, an absolute value of the dimension difference in the portion surrounded by the broken line is smaller than absolute values of the dimension differences at the remaining four points. Accordingly, the point in the broken line seems not to be the defect at a glance. On the other hand, the absolute values of the dimension differences in the portion surrounded by an alternate long and short dash line is larger than the absolute value of the dimension difference at the remaining two points. Accordingly, the points in the alternate long and short dash line seem to be the defect.

However, as can be seen from FIG. 7, the surrounding of the portion surrounded by the broken line (P2) is the region where the dimension difference becomes negative. That is, the line width in the surrounding area is smaller than the reference value. On the other hand, because the dimension difference in the portion surrounded by the broken line becomes the positive value, the portion surrounded by the broken line has the line width that is larger than the surrounding area. FIG. 9 illustrates the dimension difference from the reference value of the line width in the measured portion after the influence of the dimension distribution is removed. As can be seen from FIG. 9, the dimension difference in the portion surrounded by the broken line (P2) becomes positive, the portion surrounded by the broken line is unusually large compared with the surrounding area from the value of the positive dimension difference, and the portion surrounded by the broken line should therefore be detected as the defect.

On the other hand, as can be seen from FIG. 7, the surrounding area of the portion surrounded by the dot dash line (P1) in FIG. 8 is the region where the dimension difference becomes positive. Accordingly, in FIG. 8, the dimension difference of the portion indicates the large positive value as a result of the addition of the tendency of the line width distribution in the region. In FIG. 9, although the dimension difference of the portion surrounded by the dot dash line (P1) has the positive value, the dimension difference falls within the acceptable range, and the point should not be detected as the defect.

In the die-to-die comparison method, the chips in the regions A and B in FIG. 6 are compared to each other. The regions A and B have the contradictory tendencies of the line widths as illustrated in FIG. 7. Therefore, when the defect determination is made from the result of the dimension distribution in FIG. 8, there is a possibility that the defect to be detected cannot be detected, or the defect that need not to be detected is detected as the defect.

In the region A where the line width is increased as a whole, the dimension difference of the position where the line width is further increased indicates the large value even if the dimension difference of the position is practically acceptable. On the other hand, in the region B where the line width is decreased as a whole, the dimension difference of the position where the line width is increased indicates the small value even if the dimension difference of the position is practically unacceptable. Therefore, when the regions A and B are compared to each other, the region A indicating the large dimension difference is determined to be the defect and the region B indicating the small dimension difference is determined not to be the defect.

In such cases, the regions A and B are not compared to each other, however the cells in the region A are compared to each other, or the cells in the region B are compared to each other. That is, the cell comparison method is adopted instead of the die-to-die comparison method. In the cell comparison method, because the regions having the same tendency of the line width are compared to each other, the comparison can be performed in the state of FIG. 9 after the influence of the dimension distribution is removed. Because the defect that needs not to be detected is removed from the mask inspection result, the number of defects reviewed by the operator is decreased to shorten the inspection time. Because the number of defects described in the defect information list is also decreased, the production yield of the mask can be improved. Additionally, the defect that is hardly detected due to the influence of the dimension distribution can be detected.

As to which one of the result of the die-to-die comparison method and the result of the cell comparison method is adopted is determined according to the flowchart in FIG. 5.

In the case that the dimension measuring circuit 125 measures the pattern dimension in parallel with the acquisition of the optical image of the mask 101, the latest data is referred to in the dimension difference data measured by the dimension measuring circuit 125 when the defect is detected by the die-to-die comparison method. The dimension distribution from the position where the defect is detected to the preceding position where the dimension difference is obtained is compared to the dimension distribution in the chip and the dimension distribution among the chips (S16). As a result of the comparison, when the dimension distribution from the position where the defect is detected to the preceding position where the dimension difference is obtained is determined to fall within the predetermined range in S17 of FIG. 5, the result of the die-to-die comparison method, namely, the defect coordinate and the optical image and reference image, which are the basis of the defect determination, are stored as the mask inspection result 205 in the magnetic disk drive 109.

In the case that the dimension measuring circuit 125 measures the pattern dimension in parallel with the inspection of the comparison circuit 108, at the time when the defect is detected by the die-to-die comparison method, the dimension of the pattern in which the comparison is already performed is measured, but the dimension of the pattern in which the comparison is not performed is not measured. Therefore, in this case, the latest data is referred to from the dimension difference data measured by the dimension measuring circuit 125.

On the other hand, the defect may be detected by the die-to-die comparison method, and the dimension distribution from the position where the defect is detected to the preceding position where the dimension difference is obtained exceeds the predetermined range by comparing the dimension distribution to the dimension distribution in the chip and the dimension distribution among the chips. In this case, the result of the die-to-die comparison method is not adopted with respect to the position, but the result of the cell comparison method performed in parallel is adopted. At this point, whether the defect is detected as a result of the cell comparison method is not a problem. That is, the position determined to be the defect by the die-to-die comparison method is not registered as the defect unless the position is also determined to be the defect by the cell comparison method.

However, in the case that a cell having a repetitive pattern that could be used as a reference does not exist near the cell that becomes the inspection target, the processing is performed only by the die-to-die comparison method. In this case, even if the dimension distribution from the position where the defect is detected to the preceding position where the dimension difference is obtained exceeds the predetermined range by comparing the dimension distribution to the dimension distribution in the chip and the dimension distribution among the chips, preferably the result of the die-to-die comparison method is adopted. That is, the coordinate of the defect detected and the optical image and reference image, which are the basis of the defect determination, are stored as the mask inspection result 205 in the magnetic disk drive 109.

By way of example, the dimension distribution from the position where the defect is detected to the preceding position where the dimension difference is obtained is compared to the dimension distribution in the chip and the dimension distribution among the chips. Alternatively, the dimension distribution from the position where the defect is detected to the preceding position where the dimension difference is obtained may be compared to the dimension distribution of the region separated by the chip pitch.

For example, the dimension distribution from the position where the defect is detected to the preceding position where the dimension difference is obtained may be compared to (1) the dimension distribution in the stripe including the position determined to be the defect or (2) the dimension distribution of the chip pattern assumed from the stripe in which the dimension difference is acquired in advance of the stripe including the position determined to be the defect. Whether the dimension distribution acquired from the dimension difference measured by the dimension measuring circuit 125 falls within the predetermined range by comparing the dimension distribution to (1) the dimension distribution or (2) the dimension distribution is determined. When the dimension distribution falls within the predetermined range, the coordinate of the defect detected by the die-to-die comparison method and the optical image and reference image, which are the basis of the defect determination may be stored as the mask inspection result 205 in the magnetic disk drive 109. At this point, (1) the dimension distribution and (2) the dimension distribution are derived from the map produced by the map producing circuit 126. (1) The dimension distribution and (2) the dimension distribution can also directly be derived from the dimension difference data obtained by the dimension measuring circuit 125.

In the above modification, the defect is detected by the die-to-die comparison method, and the dimension distribution from the position where the defect is detected to the preceding position where the dimension difference is obtained is compared to (1) the dimension distribution and (2) the dimension distribution. When the dimension distribution from the position where the defect is detected to the preceding position where the dimension difference is obtained deviates from the predetermined range, the result of the die-to-die comparison method is not adopted with respect to the position, but the result of the cell comparison method performed in parallel is adopted. In this case, whether the defect is detected as a result of the cell comparison method is not a problem. That is, even the position determined to be the defect by the die-to-die comparison method is not registered as the defect unless the position is determined to be the defect by the cell comparison method. Alternatively, whether the result of the die-to-die comparison method is stored may be determined.

In the case that the cell that becomes the reference does not exist because the repetitive pattern does not exist near the cell that becomes the inspection target, the processing is performed only by the die-to-die comparison method. In this case, even if the dimension distribution from the position where the defect is detected to the preceding position where the dimension difference is obtained deviates from the predetermined range by comparing the dimension distribution to (1) the dimension distribution or (2) the dimension distribution, the result of the die-to-die comparison method is adopted. When the mask is seen as a whole, the addition of the defect that needs not to be detected to the mask inspection result is reduced, and the defect that is hardly detected due to the influence of the dimension distribution can be detected.

In the second embodiment, the control computer 110 in FIG. 1 can determine whether the result of the die-to-die method is suitably adopted by comparing the dimension distribution in the chip and the dimension distribution among the chips to the dimension distribution from the position where the defect is detected to the preceding position where the dimension difference is obtained. Alternatively, the control computer 110 may determine whether the result of the die-to-die method is suitably adopted by comparing the dimension distribution from the position where the defect is detected to the preceding position where the dimension difference is obtained to (1) the dimension distribution or (2) the dimension distribution. The control computer 110 can determine whether the result of the cell comparison method exists. In the case that not the result of the cell comparison method but only the result of the die-to-die comparison method exists, the result of the die-to-die comparison method is stored as the mask inspection result 205 in the magnetic disk drive 109 irrespective of the comparison result.

When the dimension difference obtained by the dimension measuring circuit 125 has the large degree, the position can be registered as the defect even if the position is not determined to be the defect in the comparison circuit 108. Therefore, in second embodiment, the defect determination can be made as follows.

For example, it is assumed that the threshold by which the comparison circuit 108 determines the line width defect is set to the line width dimension difference of 16 nm and the dimension ratio of 8%. The threshold of the defect determination for the measurement result of the dimension measuring circuit 125 is slightly relaxed compared with the threshold by which the comparison circuit 108 determines the line width defect, the line width dimension difference is set to 20 nm, and the dimension ratio is set to 10%. As to the predetermined range that becomes the criterion to which one of the result of the die-to-die comparison method and the result of the cell comparison method is adopted, the line width dimension difference is set to 12 nm or more, and the dimension ratio is set to 6% or more.

The result of the die-to-die comparison method is adopted, when the dimension difference obtained by the dimension measuring circuit 125 is less than 12 nm while the dimension ratio is less than 6%. On the other hand, the result of the cell comparison method is adopted, when the dimension difference obtained by the dimension measuring circuit 125 is greater than or equal to 12 nm and less than 20 nm while the dimension ratio is greater than or equal to 6% and less than 10%. The position is registered as the defect, when the dimension difference obtained by the dimension measuring circuit 125 is greater than or equal to 20 nm while the dimension ratio is greater than or equal to 10%.

The predetermined range that becomes the criterion to which one of the result of the die-to-die comparison method and the result of the cell comparison method is adopted is set in each mask that becomes the inspection target. At this point, the predetermined range is set to the range that does not exceed the threshold in the case that the position is determined to be the defect from the measured value of the dimension measuring circuit 125. The setting method is similar to the threshold setting method in the comparison circuit 108. That is, the predetermined range can individually be assigned for the case that the line width is larger than the reference data and the case that the line width is smaller than the reference data, and the predetermined range may be assigned for the case that not the line width but the inter-pattern distance is larger than the reference data and the case that the inter-pattern distance is smaller than the reference data. Additionally, the predetermined range of the hole diameter or the dimension ratio of the diameters can be assigned for the pattern having the hole shape. In this case, the predetermined range can be assigned for both the sections in the X-direction and Y-direction of the hole.

In the second embodiment, the map produced by the map producing circuit 126 can be used to transfer the pattern in the mask 101 to the wafer. For example, when the exposure apparatus that transfers the pattern in the mask 101 to the wafer can input the irradiation energy (dose) as the map, the map produced by the map producing circuit 126 is input to the exposure apparatus, and converted into the map of the irradiation energy, which allows the line width to be homogeneously transferred to the wafer. For example, in the position where the dimension difference becomes negative in the mask 101, namely, the position where the line width is thinned, the irradiation energy is adjusted such that the pattern transferred to the wafer is thickened. On the other hand, in the position where the dimension difference becomes positive in the mask 101, namely, the position where the line width is thickened, the irradiation energy is adjusted such that the pattern transferred to the wafer is thinned. Therefore, the line width of the pattern transferred to the wafer is homogenized even in the mask in which the pattern has the dimension distribution.

According to the present invention, an inspection apparatus comprises, an optical image acquisition unit that virtually divides a sample into a plurality of strip-shaped stripes along a predetermined direction to acquire an optical image of the sample in each of the stripes, a reference image producing unit that performs filtering based on design data of the chip pattern which is formed on the sample to produce a reference image corresponding to the optical image, a first comparator that compares the chip pattern of the optical image output from the optical image acquisition unit to the chip pattern of the reference image output from the reference image producing unit by a die-to-database method, a second comparator that compares repetitive pattern portions in the chip pattern of the optical image output from the optical image acquisition unit using a cell method, a dimension difference/dimension ratio acquisition unit that obtains at least one of a dimension difference and a dimension ratio between a pattern of the optical image and a pattern of the reference image compared to the pattern of the optical image by the die-to-database method, a dimension distribution acquisition unit that obtains a dimension distribution of the plurality of chip patterns from at least one of the dimension difference and the dimension ratio, which are output from the dimension difference/dimension ratio acquisition unit, and a controller that stores a result of the first comparator when, with respect to a place determined to be a defect by the comparison of the first comparator, a dimension distribution from the place to a preceding place where at least one of the dimension difference and the dimension ratio is obtained by the dimension difference/dimension ratio acquisition unit falls within a predetermined range by comparing the dimension distribution to a dimension distribution in the stripe including the place determined to be the defect or a dimension distribution of the chip pattern guessed from the stripe in which the dimension difference is acquired in advance of the stripe concerned, and stores a result of the second comparator instead of the result of the first comparator when the dimension distribution from the place determined to be the defect to the preceding place where at least one of the dimension difference and the dimension ratio is obtained by the dimension difference/dimension ratio acquisition unit exceeds the predetermined range by comparing the dimension distribution to the dimension distribution in the stripe including the place determined to be the defect or the dimension distribution of the chip pattern guessed from the stripe in which the dimension difference is acquired in advance of the stripe concerned.

The controller stores the result of the first comparator irrespective of the dimension distribution from the place determined to be the defect to the preceding place where at least one of the dimension difference and the dimension ratio is obtained by the dimension difference/dimension ratio acquisition unit, when the result of the second comparator does not exist because the repetitive pattern portion does not exist in the place determined to be the defect by the comparison of the first comparator.

Further, according to the present invention, an inspection apparatus comprises, an optical image acquisition unit that virtually divides a sample into a plurality of strip-shaped stripes along a predetermined direction to acquire an optical image of the sample in each of the stripes, a first comparator that compares the chip patterns of the optical image output from the optical image acquisition unit by a die-to-die method, a second comparator that compares repetitive pattern portions in the chip pattern of the optical image output from the optical image acquisition unit by a cell method, a dimension difference/dimension ratio acquisition unit that obtains at least one of a dimension difference and a dimension ratio between a pattern of the optical image and a pattern of the reference image compared to the pattern of the optical image by the die-to-die method, a dimension distribution acquisition unit that obtains a dimension distribution of the plurality of chip patterns from at least one of the dimension difference and the dimension ratio, which are output from the dimension difference/dimension ratio acquisition unit, and a controller that stores a result of the first comparator when, with respect to a place determined to be a defect by the comparison of the first comparator, a dimension distribution from the place to a preceding place where at least one of the dimension difference and the dimension ratio is obtained by the dimension difference/dimension ratio acquisition unit falls within a predetermined range by comparing the dimension distribution to a dimension distribution in the stripe including the place determined to be the defect or a dimension distribution of the chip pattern guessed from the stripe in which the dimension difference is acquired in advance of the stripe concerned, and stores a result of the second comparator instead of the result of the first comparator when the dimension distribution from the place determined to be the defect to the preceding place where at least one of the dimension difference and the dimension ratio is obtained by the dimension difference/dimension ratio acquisition unit exceeds the predetermined range by comparing the dimension distribution to the dimension distribution in the stripe including the place determined to be the defect or the dimension distribution of the chip pattern guessed from the stripe in which the dimension difference is acquired in advance of the stripe concerned.

The controller stores the result of the first comparator irrespective of the dimension distribution from the place determined to be the defect to the preceding place where at least one of the dimension difference and the dimension ratio is obtained by the dimension difference/dimension ratio acquisition unit, when the result of the second comparator does not exist because the repetitive pattern portion does not exist in the place determined to be the defect by the comparison of the first comparator.

The present invention is not limited to the embodiments described and can be implemented in various ways without departing from the spirit of the invention.

The above description of the present embodiment has not specified apparatus constructions, control methods, etc., which are not essential to the description of the invention, since any suitable apparatus construction, control methods, etc. can be employed to implement the invention. Further, the scope of this invention encompasses all support apparatuses employing the elements of the invention and variations thereof, which can be designed by those skilled in the art.

What is claimed is:

1. An inspection method comprising:
   virtually dividing a sample, in which a plurality of chip patterns are formed, into a plurality of strip-shaped stripes along a predetermined direction to acquire an optical image of the chip pattern in each of the stripes;
   performing filtering based on design data of the chip pattern to produce a reference image corresponding to the optical image;
   comparing the chip pattern using a die-to-database method and comparing a repetitive pattern portion in the chip pattern using a cell method;
   obtaining at least one of a dimension difference and a dimension ratio between a pattern of the optical image and a pattern of the reference image compared to the pattern of the optical image by the die-to-database method; and
   obtaining a dimension distribution of the plurality of chip patterns from at least one of the dimension difference and the dimension ratio,
   wherein, with respect to a position determined to be a defect by the comparison of the die-to-database method, a result of the die-to-database method is stored when a dimension distribution from the position to a preceding position where at least one of the dimension difference and the dimension ratio is obtained falls within a predetermined range by comparing the dimension distribution to a dimension distribution in the stripe including the position determined to be the defect, or a dimension distribution of the chip pattern assumed from the stripe in which the dimension difference is acquired in advance of the stripe concerned, and a result of the cell method is stored instead of the result of the die-to-database method when the dimension distribution from the position determined to be the defect to the preceding position where at least one of the dimension difference and the dimension ratio is obtained exceeds the predetermined range by comparing the dimension distribution to the dimension distribution in the stripe including the position determined to be the defect, or the dimension distribution of the chip pattern assumed from the stripe in which the dimension difference is acquired in advance of the stripe concerned.

2. The inspection method according to claim 1, wherein the result of the die-to-database method is stored irrespective of the dimension distribution from the position determined to be the defect to the preceding position, where at least one of the dimension difference and the dimension ratio is obtained, when the result of the cell comparison does not exist because the repetitive pattern portion does not exist in the position determined to be the defect by the comparison of the die-to-database method.

3. The inspection method according to claim 1, wherein the dimension difference is a difference in line width between the pattern of the optical image and the pattern of the reference image or a difference of a distance between the patterns of the optical image and a distance between the patterns of the reference image.

4. The inspection method according to claim 1, wherein the dimension ratio is a line width ratio of the pattern of the optical image and the pattern of the reference image, or a ratio of a distance between the patterns of the optical image and a distance between the patterns of the reference image.

5. An inspection method comprising:
   acquiring an optical image of a sample in which a plurality of chip patterns are formed;
   performing filtering based on design data of the chip pattern to produce a reference image corresponding to the optical image;
   comparing the chip pattern by a die-to-database method and comparing a repetitive pattern portion in the chip pattern by a cell method;
   obtaining at least one of a dimension difference and a dimension ratio between a pattern of the optical image, and a pattern of the reference image compared to the pattern of the optical image by the die-to-database method; and
   obtaining a dimension distribution of the plurality of chip patterns from at least one of the dimension difference and the dimension ratio,
   wherein, with respect to a position determined to be a defect by the comparison of the die-to-database method, a result of the die-to-database method is stored when a dimension distribution from the position to a preceding position where at least one of the dimension difference and the dimension ratio is obtained falls within a predetermined range by comparing the dimension distribution to a dimension distribution in a chip or a dimension distribution among chips, and a result of the cell method is stored instead of the result of the die-to-database method when the dimension distribution from the position determined to be the defect to the preceding position, where at least one of the dimension difference and the dimension ratio is obtained, exceeds the predetermined range by comparing the dimension distribution to the dimension distribution in the chip or the dimension distribution among the chips.

6. The inspection method according to claim 5, wherein the result of the die-to-database method is stored irrespective of the dimension distribution from the position determined to be the defect to the preceding position, where at least one of the dimension difference and the dimension ratio is obtained, when the result of the cell comparison does not exist because the repetitive pattern portion does not exist in the position determined to be the defect by the comparison of the die-to-database method.

7. The inspection method according to claim 5, wherein the dimension difference is a difference in line width between the pattern of the optical image and the pattern of the reference image or a difference of a distance between the patterns of the optical image and a distance between the patterns of the reference image.

8. The inspection method according to claim 5, wherein the dimension ratio is a line width ratio of the pattern of the optical image and the pattern of the reference image, or a ratio of a distance between the patterns of the optical image and a distance between the patterns of the reference image.

9. An inspection method comprising:
virtually dividing a sample in which a plurality of chip patterns are formed into a plurality of strip-shaped stripes along a predetermined direction to acquire an optical image of the chip pattern in each of the stripes;
comparing the chip pattern by a die-to-die method and comparing a repetitive pattern portion in the chip pattern by a cell method;
obtaining at least one of a dimension difference and a dimension ratio between a pattern of the optical image and a pattern of the reference image compared to the pattern of the optical image by the die-to-die method; and
obtaining a dimension distribution of the plurality of chip patterns from at least one of the dimension difference and the dimension ratio,
wherein, with respect to a position determined to be a defect by the comparison of the die-to-die method, a result of the die-to-die method is stored when a dimension distribution from the position to a preceding position where at least one of the dimension difference and the dimension ratio is obtained falls within a predetermined range by comparing the dimension distribution to a dimension distribution in the stripe including the position determined to be the defect, or a dimension distribution of the chip pattern assumed from the stripe in which the dimension difference is acquired in advance of the stripe concerned, and a result of the cell method is stored instead of the result of the die-to-die method when the dimension distribution from the position determined to be the defect to the preceding position where at least one of the dimension difference and the dimension ratio is obtained exceeds the predetermined range by comparing the dimension distribution to the dimension distribution in the stripe including the position determined to be the defect or the dimension distribution of the chip pattern assumed from the stripe in which the dimension difference is acquired in advance of the stripe concerned.

10. The inspection method according to claim 9, wherein the result of the die-to-die method is stored irrespective of the dimension distribution from the position determined to be the defect to the preceding position where at least one of the dimension difference and the dimension ratio is obtained, when the result of the cell method does not exist because the repetitive pattern portion does not exist in the position determined to be the defect by the comparison of the die-to-die method.

11. The inspection method according to claim 9, wherein the dimension difference is a difference in line width between the patterns of the optical images or a difference in distance between the patterns of the optical images.

12. The inspection method according to claim 9, wherein the dimension ratio is a line width ratio of the patterns of the optical images or a ratio of a distance between the patterns of the optical image.

* * * * *